(12) United States Patent
Wagner et al.

(10) Patent No.: US 10,918,765 B2
(45) Date of Patent: Feb. 16, 2021

(54) DECELLULARIZATION AND RECELLULARIZATION OF WHOLE ORGANS

(71) Applicant: University of Vermont and State Agricultural College, Burlington, VT (US)

(72) Inventors: Darcy Wagner, Burlington, VT (US); Daniel J. Weiss, Essex Junction, VT (US); Nicholas Bonenfant, Essex Junction, VT (US); Rachael Oldinski, Colchester, VT (US); Spencer Fenn, Rutland, VT (US)

(73) Assignee: University of Vermont and State Agricultural College, Burlington, VT (US)

( * ) Notice: Subject to any disclaimer, the term of this patent is extended or adjusted under 35 U.S.C. 154(b) by 182 days.

(21) Appl. No.: 14/783,923

(22) PCT Filed: Apr. 10, 2014

(86) PCT No.: PCT/US2014/033633
§ 371 (c)(1),
(2) Date: Oct. 12, 2015

(87) PCT Pub. No.: WO2014/169111
PCT Pub. Date: Oct. 16, 2014

(65) Prior Publication Data
US 2016/0067378 A1    Mar. 10, 2016

Related U.S. Application Data

(60) Provisional application No. 61/810,966, filed on Apr. 11, 2013.

(51) Int. Cl.
| | |
|---|---|
| *A61L 27/36* | (2006.01) |
| *A61L 27/52* | (2006.01) |
| *A61L 27/54* | (2006.01) |
| *A61F 17/00* | (2006.01) |
| *A61L 24/08* | (2006.01) |
| *A61K 9/00* | (2006.01) |
| *C09D 105/04* | (2006.01) |
| *C08B 37/00* | (2006.01) |
| *C08L 5/04* | (2006.01) |
| *A61L 27/34* | (2006.01) |
| *A61L 27/38* | (2006.01) |
| *A61L 24/00* | (2006.01) |
| *A61L 24/04* | (2006.01) |

(52) U.S. Cl.
CPC .......... *A61L 27/3604* (2013.01); *A61F 17/00* (2013.01); *A61K 9/0019* (2013.01); *A61L 24/0031* (2013.01); *A61L 24/046* (2013.01); *A61L 24/08* (2013.01); *A61L 27/34* (2013.01); *A61L 27/3687* (2013.01); *A61L 27/38* (2013.01); *A61L 27/52* (2013.01); *A61L 27/54* (2013.01); *C08B 37/0084* (2013.01); *C08L 5/04* (2013.01); *C09D 105/04* (2013.01); *A61L 2430/40* (2013.01)

(58) Field of Classification Search
CPC ........ A61L 27/20; A61L 24/08; A61L 24/046; A61L 24/0031; A61K 47/36; A61K 9/70; A61F 13/02; C08B 37/0084
See application file for complete search history.

(56) References Cited

U.S. PATENT DOCUMENTS

| | | | |
|---|---|---|---|
| 5,700,848 A | 12/1997 | Soon-Shiong et al. | |
| 5,749,895 A | 5/1998 | Sawyer et al. | |
| 5,811,814 A | 9/1998 | Leone et al. | |
| 5,851,229 A * | 12/1998 | Lentz .................... | A61L 27/20 |
| | | | 623/23.72 |
| 5,876,742 A | 3/1999 | Cochrum et al. | |
| 6,175,054 B1 | 1/2001 | Jacques | |
| 6,333,194 B1 | 12/2001 | Levy et al. | |
| 7,504,549 B2 | 3/2009 | Castellani et al. | |
| 7,858,838 B2 | 12/2010 | Holm et al. | |
| 8,269,058 B2 | 9/2012 | McCarthy et al. | |
| 8,273,373 B2 * | 9/2012 | Alsberg ................. | A61L 27/38 |
| | | | 424/484 |

(Continued)

FOREIGN PATENT DOCUMENTS

| | | | |
|---|---|---|---|
| CA | 2740597 A1 | 4/2011 | |
| CA | 2835312 A1 | 5/2014 | |

(Continued)

OTHER PUBLICATIONS

Badylak et al. "Extracellular matrix as a biological scaffold material: Structure and function" (2009), Acta Biomaterialia, vol. 5: 1-13. (Year: 2009).*
A. S. Hoffman, "Hydrogels for biomedical applications" 2002, Adv. Drug Del. Rev. 43, 3-12.

(Continued)

*Primary Examiner* — Teresa E Knight

(74) *Attorney, Agent, or Firm* — Saul Ewing Arnstein & Lehr LLP; Kathryn Doyle

(57) ABSTRACT

The present invention provides systems and methods for the decellularization and recellularization of tissue segments. In certain instances the invention comprises coating or sealing decellularized tissue segments with a cross-linked alginate hydrogel. The present invention also provides a decellularization kit, which may be used to generate decellularized tissue segments for high throughput studies. Also included are compositions and methods of tissue sealants comprising methacrylated alginate.

4 Claims, 12 Drawing Sheets

(56) References Cited

U.S. PATENT DOCUMENTS

| | | | |
|---|---|---|---|
| 8,551,933 | B2 | 10/2013 | Parrish et al. |
| 8,623,397 | B2 | 1/2014 | Ma et al. |
| 8,795,713 | B2 | 8/2014 | Makower et al. |
| 2006/0094112 | A1 | 5/2006 | Babalola et al. |
| 2007/0020248 | A1 | 1/2007 | Everaerts et al. |
| 2007/0218038 | A1* | 9/2007 | Nataraj .............. A61K 35/32 424/93.7 |
| 2007/0254005 | A1* | 11/2007 | Pathak ............... A61K 35/12 424/423 |
| 2007/0269651 | A1 | 11/2007 | Denome et al. |
| 2009/0142396 | A1 | 6/2009 | Odar et al. |
| 2009/0202977 | A1 | 8/2009 | Ott et al. |
| 2011/0269208 | A1 | 11/2011 | Burdick et al. |
| 2012/0283843 | A1 | 11/2012 | Cabrera |
| 2014/0023723 | A1* | 1/2014 | Leach ............... A61L 27/3633 424/577 |
| 2014/0155916 | A1 | 6/2014 | Hodgkinson et al. |

FOREIGN PATENT DOCUMENTS

| | | |
|---|---|---|
| WO | WO 2000/021572 | 4/2000 |
| WO | 03092754 A1 | 11/2003 |
| WO | WO 2004/032713 | 4/2004 |
| WO | 2004080343 A2 | 9/2004 |
| WO | WO 2012/149358 | 11/2012 |
| WO | WO 2013025763 | 2/2013 |
| WO | WO2013119551 | 8/2013 |
| WO | WO 2014/169111 | 10/2014 |

OTHER PUBLICATIONS

Baumann et al. "Closure of a bronchopleural fistula using decalcified human spongiosa and a fibrin sealant." Ann Thorac Surg 1997; 64:230-3.
Bonenfant et al., "The effects of storage and sterilization on de-cellularized and re-cellularized whole lung." 2013, Biomaterials 34(13):3231-45.
Bonvillain et al., "A nonhuman primate model of lung regeneration: detergent-mediated decellularization and initial in vitro recellularization with mesenchymal stem cells." 2012, Tissue Engineering Part A, 18: 2437-2452.
Daly et al., "Initial binding and recellularization of decellularized mouse lung scaffolds with bone marrow-derived mesenchymal stromal cells." 2011, Tissue Engineering Part A, 18: 1-16.
Gomes et al., "Respiratory mechanics and lung development in the rat from early age to adulthood." 2001, J. Appl Physiol, 90(5): 1631-1638.
International Search Report dated Sep. 23, 2014 for PCT/US2014/033633.
Jensen et al., "A rapid lung de-cellularization protocol supports embryonic stem cell differentiation in vitro and following implantation." 2012, Tissue Engineering Part C: Methods, 18:632-646.
Lee and Mooney, "Alginate: properties and biomedical applications." 2012, Progress in Polymer Science, 37: 106-26.
Mabry et al., "Prehospital advances in the management of severe penetrating trauma." Critical Care Medicine. 36(7 Suppl):S258-66, 2008.
McPherson et al. "Prevalence of tension pneumothorax in fatally wounded combat casualties." J Trauma 2006; 60:573-578.
Nicholas et al. "Successful use of autologous fibrin gel in traumatic bronchopleural fistula: case report." J Trauma 1992; 32:87-88.
Ohta et al., "Pleural covering method of polyglycolic acid felt with sodium alginate water solution for prevention of postoperative pulmonary fistula." Kyobu Geka—Japanese Journal of Thoracic Surgery. 61(7):561-3, 2008 (abstract).
Orens and Garrity, "General Overview of Lung Transplantation and Review of Organ Allocation." 2009, Proc Am Thorac Soc, 6: 13-19.
Sokocevic et al, "The effect of age and emphysematous and fibrotic injury on the re-cellularization of de-cellularized lungs." 2013, Biomaterials; 34(13):3256-69.
Sprung et al., "Treatment of a bronchopleural fistula with a Fogarty catheter and oxidized regenerated cellulose (surgicel)." Chest 1994; 105:1879-81.
Sun and Tan. "Alginate-Based Biomaterials for Regenerative medicine Applications." 2013, Materials 6(4):1285-1309.
Umeda "In situ tissue engineering of canine skull with guided bone regeneration" 2009, Acta Oto Laryngologica, 129: 1509-1518.
W. E. Hennink and C. F. van Nostrum, " Novel crosslinking methods to design hydrogels" 2002, Adv. Drug Del. Rev. 54, 13-36.
Wallis et al., "Comparative Assessment of Detergent-Based Protocols for Mouse Lung De-Cellularization and Re-Cellularization" 2012, Tissue Engineering Part C: Methods, 18:420-432.
Zhao et al., "Stress-relaxation behavior in gels with ionic and covalent crosslinks" 2010, Journal of Applied Physics, 107: 63509.
European Patent Application No. EP14783333—Supplementary European Search Report dated Nov. 7, 2016.
Jeon, et al., "Photocrosslinked alginate hydrogels with tunable biodegradation rates and mechanical properties." 2009, Biomaterials 30(14):2724-2734.
Nunamaker, et al., "An alginate hydrogel dura mater replacement for use with intracortical electrodes." 2010, Journal of Biomedical Materials Research Part B: Applied Biomaterials 95B(2):421-429.
Zhang, et al., "An ionically crosslinked hydrogel containing vancomycin coating on a porous scaffold for drug delivery and cell culture." 2008, International Journal of Pharmaceutics 353:(1-2)74-87.
European Patent Application No. 14783333.9—Office Action dated Sep. 14, 2018.

* cited by examiner

Method 1:
CA
crosslinking

Crosslinked Alginate

Methacrylated Sodium Alginate (AA-MA)

Method 2: UV crosslinking

UV Cross Linking

DECELLULARIZATION AND RECELLULARIZATION OF WHOLE ORGANS

CROSS-REFERENCE TO RELATED APPLICATION

This application is a U.S. national phase application filed under 35 U.S.C. § 371 claiming benefit to International Patent Application No. PCT/US2014/033633, filed on Apr. 10, 2014, which claims priority under 35 U.S.C. § 119(e) to U.S. Provisional Patent Application No. 61/810,966, filed on Apr. 11, 2013, each of which application is hereby incorporated herein by reference in its entirety.

STATEMENT REGARDING FEDERALLY SPONSORED RESEARCH OR DEVELOPMENT

This invention was made with government support under HL106625; HL108689; HL094611; RR155557; and HL076122, awarded by the National Institutes of Health. The government has certain rights in the invention.

BACKGROUND OF THE INVENTION

It is estimated that about 1,000-1,500 lung transplants are performed per year in the United States (Orens and Garrity, 2009, Proc Am Thorac Soc, 6: 13-19). The indications are diverse but there is a significant shortage of suitable donor lungs, and unfortunately, many on waiting lists die before a lung becomes available (Orens and Garrity, 2009, Proc Am Thorac Soc, 6: 13-19). Further, lung transplantation requires lifelong immunosuppression, and the 5 year mortality after transplantation is approximately 50% (Orens and Garrity, 2009, Proc Am Thorac Soc, 6: 13-19).

While some cadaveric organs, such as kidneys, have been successfully utilized for many years, this has not yet been feasible with other organ types, such as cadaveric lungs. One potential strategy considered is to utilize decellularized whole lungs as scaffolds for seeding with autologous cells obtained from eventual transplant recipients, and to grow functional lung tissue ex vivo. This approach has provided exciting initial results (Daly et al., 2012, Tissue Engineering Part A, 18: 1-16; Wallis et al., 2012, Tissue Engineering Part C: Methods, 18:420-432; Bonenfant et al, Biomaterials; Sokocevic et al, Biomaterials; Bonvillain et al., 2012, Tissue Engineering Part A, 18: 2437-2452; Jensen et al., 2012, Tissue Engineering Part C: Methods, 18:632-646). Further, these decellularized scaffolds provide a powerful tool in which to investigate lung biology, including the interaction of lung epithelial and other cells with the extracellular matrix (ECM) proteins in the scaffold, as well as the effect of environmental influences, such as oxygen tension, stretch/strain and shear forces, on lung cell behavior.

As mouse and rat lungs are readily available and easily handled, effective high-throughput approaches can be utilized to assess the effects of multiple growth and environmental conditions on lung de- and recellularization. However, a more limited supply of human lungs and the practical aspects of handling these organs impede comparable rapid and effective high throughput study. There is also a tremendous wastage of human lungs that could be used for pre-clinical bioengineering studies. The development of novel and innovative techniques to dissect out multiple small lung segments (~1-3 cm$^3$) from individual cadaveric or donor lungs unsuitable for transplant that retain 3-dimensional structure, and that can be ventilated and perfused, is vital for developing a high-throughput studies of human and other large animal lungs.

Approaches to promote healing of injuries to connective or pleural tissue are also inadequate. Injury to the connective tissue that lines the lung, the pleura, or to the lung itself can occur from many causes including trauma, as well as underlying lung disease such as emphysema, cystic fibrosis, pulmonary fibrosis, pulmonary infections, or lung cancers. Mechanical ventilation of critically ill patients in operating rooms and intensive care units is another significant cause of pleural damage. The result of these injuries is that air (or liquid) accumulates outside of the lung but remains inside the chest cavity compressing the lungs and heart causing a condition known as pneumothorax (or hydrothorax). The resulting lung collapse can be partial and asymptomatic or can be complete and instantly life-threatening (tension pneumothorax). Another example of major pleural-associated mortality and morbidity is malignant pleural effusion, a continuous leak of fluid into the pleural space from cancer-damaged lungs.

Pneumo (hydro)thoraces and pleural effusions are generally treated by placement of a tube into the chest cavity that drains out the leaked air or fluid allowing the lung to re-expand and the underlying injury to heal. However, the nature of the underlying trauma and/or the underlying disease may not allow adequate healing and the air leak can continue. This can result in rapid mortality, for example in a battlefield or other trauma settings such as a motor vehicle accident, or can result in prolonged need for chest tube drainage with significantly increased morbidity, mortality, hospital stays, health care costs, and other complications (bronchopleural fistulas). Bronchopleural fistulas (persistent, abnormal connection between the lung airways and the pleural space) are extremely difficult to treat and at present, apart from surgical interventions or pleurodesis (chemical or mechanical adhesion of the pleural surfaces), both often unsuccessful. There is no effective means of patching the injury to stop the air or fluid leak and allow appropriate healing to occur. Malignant pleural effusions are similarly difficult to treat.

Bronchopleural fistulas, malignant pleural effusions, and traumatic or ventilator-induced pleural injuries are a continuing source of morbidity, mortality, extended hospitalizations, and increased health care expenditures. Notably, tension pneumothorax and traumatic lung injury represents the second leading cause of potentially preventable battlefield deaths, resulting in an estimated 3% to 4% of all fatal injuries.

Current management approaches center on prolonged chest tube drainage and hope for eventual lung healing. Unmodified alginate or modified polyethylene glycol (PEG) hydrogel to repair clinical pleural defects have failed to gain traction in the clinic, as unmodified alginate is ineffective and PEG is cost prohibitive. Surgical intervention and/or pleurodesis are frequently ineffective and may worsen the underlying bronchopleural fistulas or other problems. Other approaches such as use of fibrin glue or cyanoacrylates (super glue) have also been unsuccessful as these do not adequately adhere to lung surfaces or have inadequate tensile properties.

Thus, there is a need in the art for compositions and methods for the production of biologically relevant organ constructs and effective treatments promote healing to overcome the limitations of the aforementioned approaches.

SUMMARY OF THE INVENTION

The present invention provides compositions, methods, and kits for the production of decellularized tissue constructs and their subsequent recellularization. Also included are compositions and methods with methacrylated alginate to form a non-toxic, flexible tissue seal that provides tensile strength and durability, such as for repairing bronchopleural fistulas or malignant pleural effusions where pleurodesis is unsuccessful.

In one aspect, the invention includes a method of recellularizing a decellularized biological tissue, comprising the steps of coating at least a portion of a decellularized biological tissue with a hydrogel sealing agent; and contacting the decellularized biological tissue with at least one cell type.

In another aspect, the invention includes a method for sealing a wound in a mammal comprising applying a methacrylated alginate sealing agent to the wound.

In yet another aspect, the invention includes a tissue sealant comprising methacrylated alginate.

In still yet another aspect, the invention includes a use of a methacrylated alginate sealing agent for sealing a wound.

Another aspect of the invention includes a methacrylated alginate sealing agent for use as a tissue sealant.

Still another aspect of the invention includes a kit for recellularizing a decellularized biological tissue, comprising at least one reagent for decellularizing a biological tissue; at least one sealing agent; and instructions for decellularizing a biological tissue, applying the at least one sealing agent to at least a portion of the decellularized biological tissue, and contacting the decellularized biological tissue with at least one cell type.

Still yet another aspect of the invention includes a system for coating a tissue scaffold, comprising a tissue scaffold; a methacrylated alginate solution, wherein the methacrylated alginate solution is applied to at least a portion of the tissue scaffold surface; and an agent for crosslinking the methacrylated alginate solution, wherein at least one property of the methacrylated alginate solution is controlled by the degree of alginate methacrylation.

In various embodiments of the above aspects or any other aspect of the invention delineated herein, the invention includes the hydrogel sealing agent or hydrogel solution comprises alginate. In another embodiment, the hydrogel sealing agent or hydrogel solution comprises methacrylated alginate. In yet another embodiment, the alginate is methacrylated at one, two, or four methacrylation sites. In still yet another embodiment, at least one property of the sealing agent is controlled by the degree of alginate methacrylation. In still yet another embodiment, at least one property of the sealing agent is controlled by the degree of methacrylated alginate crosslinking.

In one embodiment, the sealing agent further comprises a crosslinking solution or agent. In another embodiment, the crosslinking solution comprises calcium chloride. In yet another embodiment, the crosslinking agent is selected from the group consisting of calcium chloride; ammonium persulfate (APS) and tetramethylethylenediamine (TEMED), glutaraldehyde, epoxides, oxidized dextran, p-azidobenzoyl hydrazide, N-[α.-maleimidoacetoxy]succinimide ester, p-azidophenyl glyoxal monohydrate, bis[β-(4-azidosalicylamido)ethyl]disulfide, bis[sulfosuccinimidyl]suberate, dithiobis[succinimidyl proprionate, disuccinimidyl suberate, 1-ethyl-3-[3-dimethylaminopropyl]carbodiimide hydrochloride (EDC), N-hydroxysuccinimide (NHS), visible light irradiation, ultraviolet irradiation, and combinations thereof. In another embodiment, the crosslinking agent comprises ultraviolet radiation. In yet another embodiment, at least one property of the sealing agent is controlled by the degree of alginate crosslinking.

In various other embodiments of the above aspects or any other aspect of the invention delineated herein, the methacrylated alginate sealing agent further comprises a therapeutic agent or biological agent selected from the list consisting of a nucleic acid, an antibiotic, an anti-inflammatory agent, a growth factor, a cytokine, a enzyme, a protein, a peptide, at least one amino acid, a carbohydrate, a lipid, a hormone, a microsome, one or more cells, a derivative or a variation thereof, and any combination thereof.

In various other embodiments of the above aspects or any other aspect of the invention delineated herein, at least one sealing agent comprises a hydrogel solution. In one embodiment, the hydrogel solution comprises alginate. In another embodiment, the hydrogel solution comprises methacrylated alginate.

In another embodiment, the methacrylated alginate is ionically or covalently crosslinked. In yet another embodiment, at least one property of the methacrylated alginate solution is controlled by the degree of methacrylated alginate crosslinking. In still yet another embodiment, the methacrylated alginate is formulated in a liquid or in a solid. In another embodiment, the solid is hydrated after application to the wound. In embodiments when the methacrylated alginate is formulated in a liquid or in a solid, the application further comprises crosslinking the methacrylated alginate to form a hydrogel.

In various other embodiments of the above aspects or any other aspect of the invention delineated herein, the invention includes determining whether a residual decellularization reagent is present on the decellularized biological tissue. In another embodiment, the invention includes removing the residual decellularization reagent when the presence of the decellularization reagent on the biological tissue is detected. In yet another embodiment, the invention includes exposing the methacrylated alginate sealing agent to a crosslinking agent.

In some embodiments, the application further comprises crosslinking the methacrylated alginate. In one embodiment, the application of methacrylated alginate comprises injecting the methacrylated alginate through a catheter. In another embodiment, the application further comprises crosslinking the methacrylated alginate. In yet another embodiment, the catheter is a fiber optic catheter capable of pulsing the methacrylated alginate with visible light.

In yet another embodiment, the invention further includes an assay for detecting the presence of the at least one reagent on the decellularized tissue.

In another embodiment, the tissue scaffold is a decellularized biological tissue. In yet another embodiment, the decellularized biological tissue is lung tissue. In still yet another embodiment, the methacrylated alginate solution forms an artificial pleura.

In still yet another embodiment, the invention further includes at least one cell type positioned on or in the decellularized lung tissue.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 4A through FIG. 4C, is a set of images depicting the alginate coating and seeding of decellularized human lungs. A) Artificial pleura has adhered to the outside periphery of the de-cellularized human lung segment (arrows). B) human pulmonary vascular endothelial cells following vascular inoculation; C) Human bronchial epithelial (HBE) cells following airway inoculation. a=airways, bv=blood vessels. Orig Mags A: 100×; B,C: 200×.

DETAILED DESCRIPTION

Figure 1A:
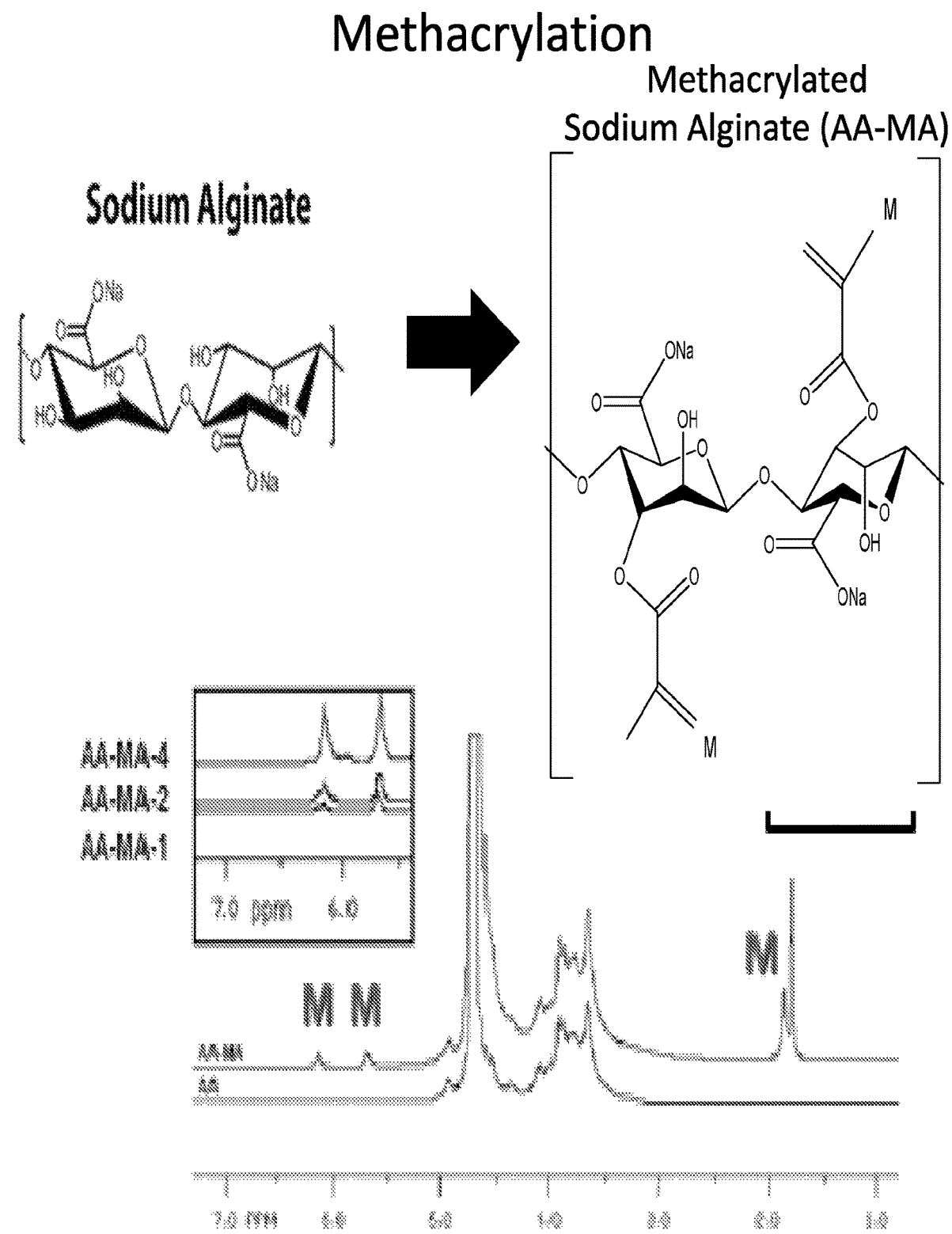
FIG. 1A depicts the production of methacrylated sodium alginate and the viscosity of sodium alginate solution. The $^1$H-NMR spectra of methacrylated alginate (AA-MA) and AA in $D_2O$ at 25° C. confirms differing degrees of methacrylation. AA has four possible methacrylation sites (at hydroxyls, OH)-AA-MA-1 has one site methacrylated, AA-MA-2 has two, AA-MA-4 has all four. Peaks corresponding to the presence of methacrylate groups are labeled "M." Controlling the degree of methacrylation permits different degrees of crosslinking via radical polymerization upon exposure to UV in the presence of a photoinitiator.

The present invention provides compositions, methods, and kits for the production of decellularized tissue constructs and their subsequent recellularization. In certain embodiments, the decellularized tissue constructs of the invention are used for high-throughput studies of organ recellularization, organ physiology, and/or organ pathology. In one embodiment, the composition of the invention comprises a decellularized tissue construct coated with a hydrogel. The hydrogel coating prevents leakage and permits effective recellularization of the construct. In certain embodiments, the hydrogel comprises crosslinked sodium alginate. In one embodiment, the invention comprises a kit comprising reagents required for the production of decellularized tissue constructs. In one embodiment, the kit comprises reagents for decellularization, an assay to measure the presence and/or amount of residual toxic detergent, and reagents for coating the decellularized construct with a hydrogel.

Definitions

Unless defined otherwise, all technical and scientific terms used herein have the same meaning as commonly understood by one of ordinary skill in the art. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, or ±5%, or 1%, or ±0.1% from the specified value, as such variations are appropriate.

As used herein, to "alleviate" a disease, defect, disorder or condition means reducing the severity of one or more symptoms of the disease, defect, disorder or condition.

By "alginate" is meant a polysaccharide comprising copolymer chains of mannuronic acid and guluronic acid, extracted from brown algae, as well as physically, chemically and/or enzymatically derivatized forms thereof.

As used herein, "autologous" refers to a biological material derived from the same individual into whom the material will later be re-introduced.

As used herein, "allogeneic" refers to a biological material derived from a genetically different individual of the same species as the individual into whom the material will be introduced.

As used here, "biocompatible" refers to any material, which, when implanted in a mammal, does not provoke an adverse response in the mammal. A biocompatible material, when introduced into an individual, is not toxic or injurious to that individual, nor does it induce immunological rejection of the material in the mammal.

As used herein, the terms "biocompatible polymer" and "biocompatibility" when used in relation to polymers are recognized in the art. For example, biocompatible polymers include polymers that are generally neither toxic to the host, nor degrade (if the polymer degrades) at a rate that produces monomeric or oligomeric subunits or other byproducts at toxic concentrations in the host. In one embodiment, biodegradation generally involves degradation of the polymer in a host, e.g., into its monomeric subunits, which may be known to be effectively non-toxic. Intermediate oligomeric products resulting from such degradation may have different toxicological properties, however, or biodegradation may involve oxidation or other biochemical reactions that generate molecules other than monomeric subunits of the polymer. Consequently, in one embodiment, toxicology of a biodegradable polymer intended for in vivo use, such as implantation or injection into a patient, may be determined after one or more toxicity analyses. It is not necessary that any subject composition have a purity of 100% to be deemed biocompatible; indeed, it is only necessary that the subject compositions be biocompatible as set forth above. Hence, a subject composition may comprise polymers comprising 99%, 98%, 97%, 96%, 95%, 90%, 85%, 80%, 75% or even less of biocompatible polymers, e.g., including polymers and other materials and excipients described herein, and still be biocompatible.

The term "biologically compatible carrier" or "biologically compatible medium" refers to reagents, cells, compounds, materials, compositions, and/or dosage formulations which are suitable for use in contact with the tissues of human beings and animals without excessive toxicity, irritation, allergic response, or other complication commensurate with a reasonable benefit/risk ratio.

By "crosslinking" is meant creating a bond that links one polymer chain to another. Crosslinking may be induced through a crosslinking agent or source or may be induced through self-assembly.

By "crosslinking agent" or "crosslinking source" is meant an agent that is capable of forming a chemical or ionic links between molecules. Non-limiting examples of crosslinking agents or sources include calcium chloride; ammonium persulfate (APS) and tetramethylethylenediamine (TEMED), glutaraldehyde, epoxides, oxidized dextran, p-azidobenzoyl hydrazide, N-[α.-maleimidoacetoxy]succinimide ester, p-azidophenyl glyoxal monohydrate, bis-[β-(4-azidosalicylamido)ethyl]disulfide, bis[sulfosuccinimidyl]suberate, dithiobis[succinimidyl proprionate, disuccinimidyl suberate, 1-ethyl-3-P-dimethylaminopropyl]carbodiimide hydrochloride (EDC), N-hydroxysuccinimide (NHS), riboflavin, heat, visible light irradiation, ultraviolet irradiation, blue light irradiation, and combinations thereof.

By "crosslinking solution" is meant a crosslinking agent in a solution or solvent.

By "degree of alginate crosslinking" or "degree of methacrylated alginate crosslinking" is meant the amount of polymerization of alginate or methacrylated alginate molecules.

"Photocrosslinking" refers to bond formation that links one polymer chain to another upon exposure to light of appropriate wavelengths. For example, two polymers conjugated to a photoreactive group can be covalently photocrosslinked by covalent bond formation between the photoreactive groups.

The term "decellularized" or "decellularization" as used herein refers to a biostructure (e.g., an organ, or part of an organ, or a tissue), from which the cellular content has been removed leaving behind an intact acellular infra-structure. Some organs are composed of various specialized tissues. The specialized tissue structures of an organ, or parenchyma, provide the specific function associated with the organ. The supporting fibrous network of the organ is the stroma. Most organs have a stromal framework composed of unspecialized connecting tissue which supports the specialized tissue. The process of decellularization removes the specialized tissue cells, leaving behind the complex three-dimensional network of extracellular matrix. The connective tissue infra-structure is primarily composed of collagen. The decellularized structure provides a biocompatible substrate onto which different cell populations can be infused. Decellularized biostructures can be rigid, or semi-rigid, having an ability to alter their shapes.

The term "derived from" is used herein to mean to originate from a specified source.

As used herein, "extracellular matrix composition" includes both soluble and non-soluble fractions or any portion thereof. The non-soluble fraction includes those secreted ECM proteins and biological components that are deposited on the support or scaffold. The soluble fraction includes refers to culture media in which cells have been cultured and into which the cells have secreted active agent(s) and includes those proteins and biological components not deposited on the scaffold. Both fractions may be collected, and optionally further processed, and used individually or in combination in a variety of applications as described herein.

As used herein, the term "gel" refers to a three-dimensional polymeric structure that itself is insoluble in a particular liquid but which is capable of absorbing and retaining large quantities of the liquid to form a stable, often soft and pliable, but always to one degree or another shape-retentive, structure. When the liquid is primarily water, the gel is referred to as a hydrogel.

As used herein, a "graft" refers to a composition that is implanted into an individual, typically to replace, correct or otherwise overcome a cell, tissue, or organ defect. A graft may comprise a scaffold. In certain embodiments, a graft comprises decellularized tissue. In some embodiments, the graft may comprise a cell, tissue, or organ. The graft may consist of cells or tissue that originate from the same individual; this graft is referred to herein by the following interchangeable terms: "autograft," "autologous transplant," "autologous implant," and "autologous graft." A graft comprising cells or tissue from a genetically different individual of the same species is referred to herein by the following interchangeable terms: "allograft," "allogeneic transplant," "allogeneic implant," and "allogeneic graft." A graft from an individual to his identical twin is referred to herein as an "isograft," a "syngeneic transplant," a "syngeneic implant," or a "syngeneic graft." A "xenograft," "xenogeneic transplant," or "xenogeneic implant" refers to a graft from one individual to another of a different species.

By "hydrated after application" is meant the solid sealing agent is capable of absorbing fluid from the surrounding tissues at the site of application or from exogenous liquid to hydrate the sealing agent to liquid form.

By "hydrogel sealing agent" is meant a sealing agent in liquid or fluid form with at least one polymer chain crosslinked to another to form a multi-dimensional polymeric structure.

As used herein, the term "intact" refers to a state of being whereby an element is capable of performing its original function to a substantial extent.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the polysaccharide or copolymer or cause other adverse consequences. That is, a polysaccharide or copolymer of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "methacrylation" or "methacrylated" is meant a modification by adding a methacrylate functional group capable of covalent crosslinking by free radical polymerization. The methacrylate moiety comprises either a carbon-carbon double bond (such as acrylic acid, methacrylic acid, and corresponding acid chlorides and anhydrides) or a triple bond capable of free radical polymerization. Ester linkages are often employed to bond a polysaccharide (ie. alginate) to the polymerizable moiety (i.e. methacryl).

By "degree of alginate methacrylation" is meant number of methacrylate groups added to alginate. Varying levels of methacrylation may be achieved by varying the ratio of alginate to methacrylic anhydride. In some embodiments, the alginate is methacrylated at one, two, three, four, or more sites. The polymerization may be initiated by light or other forms of energy including, but not limited to, thermal, ultrasonic, and gamma radiation using appropriate initiators, including but not limited to, 2,2-dimethoxy-2-phenyl acetophenone or its water soluble derivatives.

By "patch" is meant a crosslinked sealing agent at a target site. Application of the sealing agent to the target site, either as a liquid or a solid hydrated at the target site and crosslinking of the sealing agent creates a patch. The patch is a sutureless closure at the target site or tissue cover over the target site.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutical composition" or "pharmaceutically acceptable composition" refers to a mixture of at least one compound or molecule useful within the invention with a pharmaceutically acceptable carrier. The pharmaceutical composition facilitates administration of the compound or molecule to a patient. Multiple techniques of administering a compound or molecule exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound or molecule useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other nontoxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound or molecule useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "polymerization" or "crosslinking" refers to at least one reaction that consumes at least one functional group in a monomeric molecule (or monomer), oligomeric molecule (or oligomer) or polymeric molecule (or polymer), to create at least one chemical linkage between at least two distinct molecules (e.g., intermolecular bond), at least one chemical linkage within the same molecule (e.g., intramolecular bond), or any combination thereof. A polymerization or crosslinking reaction may consume between about 0% and about 100% of the at least one functional group available in the system. In one embodiment, polymerization or crosslinking of at least one functional group results in about 100% consumption of the at least one functional group. In another embodiment, polymerization or crosslinking of at least one functional group results in less than about 100% consumption of the at least one functional group.

As used herein, "scaffold" refers to a structure, comprising a biocompatible material that provides a surface suitable for adherence and proliferation of cells. A scaffold may further provide mechanical stability and support. A scaffold may be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

By "sealing agent" is meant an agent that provides a sutureless closure or tissue cover in a region where mechanical integrity of the tissue is compromised and it can be in the form of a liquid or a solid capable of being hydrated to liquid form. In an exemplary embodiment, the sealing agent comprises alginate or methacrylated alginate.

As used herein, to "treat" means reducing the frequency with which symptoms of a disease, defect, disorder, or adverse condition, and the like, are experienced by a patient.

The term "tissue," as used herein includes, but is not limited to, bone, neural tissue, fibrous connective tissue including tendons and ligaments, cartilage, dura, pericardia, muscle, lung, heart valves, veins and arteries and other vasculature, dermis, adipose tissue, or glandular tissue.

As used herein, the terms "subject" and "patient" are used interchangeably. As used herein, a subject is preferably a mammal such as a non-primate (e.g., cows, pigs, horses, cats, dogs, rats, etc.) and a primate (e.g., monkey and human), most preferably a human.

As used herein, the term "treating a disease or disorder" means reducing the frequency with which a symptom of the disease or disorder is experienced by a patient. Disease and disorder are used interchangeably herein.

As used herein, the term "therapeutically effective amount" refers to an amount that is sufficient or effective to prevent or treat (delay or prevent the onset of, prevent the progression of, inhibit, decrease or reverse) a disease or condition described or contemplated herein, including alleviating symptoms of such disease or condition.

As used herein, the term "effective amount" or "therapeutically effective amount" of a compound is that amount of compound that is sufficient to provide a beneficial effect to the subject to which the compound is administered.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention includes compositions, methods, and kits for the production of decellularized tissue constructs and their subsequent recellularization. Also included are compositions and methods with methacrylated alginate used to form a non-toxic, flexible tissue seal that provides tensile strength and durability, such as for repairing bronchopleural fistulas or malignant pleural effusions where pleurodesis is unsuccessful.

In one embodiment, the decellularized tissue constructs of the invention are derived from whole organs from large animals, including, for example, humans. In one embodiment, the decellularized constructs of the invention are decellularized lung constructs. While the description of the invention is exemplified for the production of decellularized lung constructs, a skilled artisan would recognize that the present invention is not limited to the lung. Rather, the compositions, methods, and kits of the present invention are suitable for the decellularization and/or recellularization of any biological tissue or organ.

In one embodiment, the present invention provides for the production of small decellularized tissue constructs for use in high-throughput studies. In one embodiment, the decellularized constructs of the invention retain three-dimensional structure. These small decellularized constructs may be used, for example, in studies examining the effects of mechanical, pharmacological, biochemical, and environmental conditions on tissue decellularization and/or recellularization. In certain embodiments, the constructs are small decellularized lung constructs. In one embodiment, the decellularized lung constructs are capable of being ventilated and perfused.

The development of small decellularized lung constructs is vital for developing high-throughput studies of human and other large animal lungs. However, a number of technical hurdles must be overcome to effectively produce decellularized lung tissue constructs. First and foremost, an effective, artificial pleural coating must be developed. This is necessary because decellularized lungs often leak, as the pleura can be damaged during the decellularization procedure. Dissection of individual lung segments further damages the remaining pleura, as vascular and airway branches become exposed and the integrity of the segment used for cell inoculations, ventilation, and perfusion is compromised. Thus, those examining recellularization of the constructs are left with two sub-optimal choices: 1) recellularization of an entire lung lobe while accepting a possible degree of leak, or 2) recellularization of an excised subsegment of the lung. The first (whole lung) option does not lend itself to 'high throughput' investigations required to screen multiple recellularization conditions, while recellularization in the second method (lung sections) is generally ineffective without an intact pleural covering. Thus, study of decellularization and recellularization in large animal models has been significantly hampered by this dilemma. Accordingly, the present invention comprises compositions, methods, and kits for providing a functional pleural coating in the recellularization of a decellularized tissue scaffold.

In one embodiment, the invention provides a decellularization and recellularization kit. The kit comprises reagents necessary to produce decellularized tissue constructs. For example, the kit comprises compositions and/or reagents to perform at least one of 1) decellularization of isolated tissue; 2) the dissection of decellularized tissue sections; 3) the measurement of the presence and/or amount of residual toxic detergent; and 4) the coating of the decellularized tissue.

Hydrogel Coating

In one embodiment, the composition of the invention comprises a decellularized tissue construct coated with a hydrogel. As described herein, coating of a decellularized tissue with a hydrogel prevents leaks and permits effective recellularization. In certain embodiments, the hydrogel coating serves as an artificial pleura.

In one embodiment, the present invention provides for production of an artificial pleura coating of tissue constructs. In one embodiment, the artificial pleura comprises a hydrogel.

In one embodiment, the present invention provides a hydrogel sealing agent. The hydrogel sealing agent may be applied to a portion of tissue in order to provide a sutureless closure or tissue cover in a region where mechanical integrity of the tissue is compromised. In one embodiment, the sealing agent is a pleural lung seal. However, the hydrogel sealing agent of the invention may be used on any tissue, including decellularized tissue and non-decellularized tissue. For example, in one embodiment, the sealing agent may be used to correct a tissue defect. In one embodiment the sealing agent can be used to seal a wound. In one embodiment, the sealing agent can be used in a surgical setting to seal a tissue defect in an internal tissue.

The sealant agent may have broader applicability to a range of other native and decellularized organs and tissues. Examples include but are not limited to diseased or injured cardiac (infarct with wall thinning or rupture), and intestinal (perforation) tissues, kidney, liver, pancreas, stomach, bladder, and other organs. This approach may also be effective in traumatic injuries, including battlefield injuries. The sealing agent or the hydrogel comprising methacrylated alginate may be modified for use in any given tissue or organ to best match the specific requirements for that tissue or organ.

The hydrogel may comprise any biopolymer or synthetic polymer known in the art. For example, the hydrogel may comprise hyaluronans, chitosans, alginates, collagen, dextran, pectin, carrageenan, polylysine, gelatin or agarose. (see: W. E. Hennink and C. F. van Nostrum, 2002, Adv. Drug Del. Rev. 54, 13-36 and A. S. Hoffman, 2002, Adv. Drug Del. Rev. 43, 3-12). These materials consist of high-molecular weight backbone chains made of linear or branched polysaccharides or polypeptides. Examples of hydrogels based on synthetic polymers include but are not limited to (meth)acrylate-oligolactide-PEO-oligolactide-(meth)acrylate, poly(ethylene glycol) (PEO), poly(propylene glycol) (PPO), PEO-PPO-PEO copolymers (Pluronics), poly(phosphazene), poly(methacrylates), poly(N-vinylpyrrolidone), PL(G)A-PEO-PL(G)A copolymers, poly(ethylene imine), etc. (see A. S Hoffman, 2002 Adv. Drug Del. Rev, 43, 3-12).

In one embodiment, the alginate sealing agent may comprise modifications with functional moieties, such as but not limited to isothiocyanates, isocyanates, acyl azides, N-hydroxyl-succinimide (NHS) esters, sulfonyl chlorides, aldehydes, glyoxals, epoxides, oxiranes, carbonates, aryl halides, imidoesters, carbodiimides, anhydrides, and fluorophenyl esters.

In certain embodiments, the sealing agent of the invention is crosslinked Crosslinking of the pleural sealing agent may, in certain embodiments, provide for increased mechanical strength. Crosslinking of the sealing agent may be performed using any suitable method known in the art. In certain embodiments, one or more multifunctional cross-linking agents may be utilized as reactive moieties that covalently link biopolymers or synthetic polymers. Such bifunctional cross-linking agents may include glutaraldehyde, epoxides (e.g., bis-oxiranes), oxidized dextran, p-azidobenzoyl hydrazide, N-[α.-maleimidoacetoxy]succinimide ester, p-azidophenyl glyoxal monohydrate, bis-[β-(4-azidosalicylamido)ethyl]disulfide, bis[sulfosuccinimidyl]suberate, dithiobis[succinimidyl proprionate, disuccinimidyl suberate, 1-ethyl-3-[3-dimethylaminopropyl]carbodiimide hydrochloride (EDC), N-hydroxysuccinimide (NHS) and other bifunctional cross-linking reagents known to those skilled in the art. In certain embodiments, the sealing agent comprises a photo-activated crosslinking agent. In one embodiment, one or more components of the sealing agent is cross-linked upon exposure to UV light.

As described herein, in one embodiment, the present invention demonstrates that crosslinked alginate hydrogels provide a functional interim artificial pleura as the segments recellularize, including reconstitution of native pleura. For example, in one embodiment, at least one of alginate and methacrylated alginate are cross-linked to form an effective hydrogel coating for decellularized lung segments. In certain embodiments, alginate can be cross-linked using differential calcium chloride concentrations or a salt solution comprising a divalent cation.

In certain embodiments, methacrylated alginate can be cross-linked using exemplary methods including, but not limited to, using differential calcium chloride, ammonium persulfate (APS) and tetramethylethylenediamine (TEMED), visible or blue light irradiation, UV irradiation dosing, thermal setting, self-assembly, and combinations thereof. This approach allows for generating an artificial pleura for use in studying recellularization of decellularized lung segments. In one embodiment, the crosslinked alginate does not effectively activate macrophages, thereby minimizing immune response. As described elsewhere herein, the crosslinked alginate coating, serving as an artificial pleura, increases recellularization of decellularized tissue constructs. Thus, the hydrogel coated decellularized tissue constructs of the invention serve as effective constructs for high-throughput studies of recellularization and tissue function.

In one embodiment, the patch or sealing agent of the invention comprises a two-part composition, whereby a viscous solution is first applied via syringe to the organ or tissue of interest. After solution I has set, solution II (a cross-linking solution) is then applied and the region becomes sealed or encased.

To maximize study and use of the larger lungs, a number of different approaches to develop a practical artificial pleural coating and eliminate leak have been evaluated. Silicone, latex, and agar coatings have all proven ineffective as the solvents in which silicone and latex are traditionally dissolved in are toxic. With use of agar, the majority of subsequently inoculated cells were found embedded in the agar coating rather than remaining in the lung. Further, agar-based coatings are relatively inflexible and do not allow for appropriate ventilation.

In some embodiments, at least one agent, such as a therapeutic agent or biological agent, can be administered or delivered with the sealing agent to aid in healing of the wound or growth of the cells at the target site. The therapeutic agent or biological agent includes, but is not limited to, nucleic acids, an antibiotic, an anti-inflammatory agent, a growth factor, a cytokine, a enzyme, a protein, peptides, amino acids, carbohydrate, lipid, hormone, microsome, one or more cell types, derivatives and variations thereof, and any combination thereof. The therapeutic agent or biological agent can be in a mixture with the sealing agent or applied separately before or after the sealing agent to the target site. For example, the therapeutic agent or biological agent can be included in a liquid mixture with the sealing agent. This would allow the therapeutic agent or biological agent and sealing agent to be applied simultaneously to the target site. The agent can also be applied separately before or after the sealing agent. To preserve the integrity of therapeutic agents or biological agents that are sensitive to crosslinking agents, such as UV irradiation, can be applied after the sealing agent has been crosslinked. In one embodiment, the tissue sealant further comprises at least one therapeutic agent or biological agent.

Physico-Mechanical Properties and Controlled Methacrylation of Alginate

Chemical modification of alginate has been studied extensively for improving upon the physical and mechanical properties of ionically crosslinked alginate gels (Zhao et al., 2010, Journal of Applied Physics, 107: 63509-5; Lee and Mooney 2012, Progress in Polymer Science, 37: 106-26). Methacrylation of alginate imparts a functional group capable of covalent crosslinking by free radical polymerization. The moiety contains either a carbon-carbon double bond (such as acrylic acid, methacrylic acid, and corresponding acid chlorides and anhydrides) or a triple bond capable of free radical polymerization. Ester linkages are often employed to bond a polysaccharide (ie. alginate) to the polymerizable moiety (ie. methacryl). The degree of methacrylation of the alginate can be achieved by varying the ratio of alginate to methacrylic anhydride. The polymerization may be initiated by light or other forms of energy including, but not limited to, thermal, ultrasonic, and gamma radiation using appropriate initiators, including but not limited to, 2,2-dimethoxy-2-phenyl acetophenone or its water soluble derivatives.

The traditional, aqueous-based methods for methacrylating alginate are generally unable to reliably control the degree of methacrylation and often result in low degrees of methacrylation. As contemplated herein, the ability to tailor the mechanical properties of the final material hinges on controlling the degree of methacrylation in the alginate precursor material.

Therefore, in addition to the aforementioned biological criteria for a synthetic pleura material, an artificial pleura needs to have suitable mechanical properties for high throughput studies for ventilation and perfusion. In one embodiment, the present invention includes controlling the degree of alginate methacrylation, which allows for control of the degree of cross-linking, and thereby permitting control of the mechanical properties of the resulting coated and recellularized tissue. For example, in certain embodiments, the invention comprises methacrylation of alginate in dimethyl sulfoxide (DMSO).

In one embodiment, the invention provides an optimal alginate solution having a controlled viscosity. For example, the viscosity of the alginate solution may be varied by controlling the concentration of alginate, or by increasing the molecular weight of the polymer while maintaining alginate concentration (w/v).

Crosslinking of the alginate sealing agent may comprise any method of crosslinking known in the art. In one embodiment, the alginate sealing agent of the artificial pleura comprises sodium alginate, where the sodium alginate is crosslinked with calcium chloride. In one embodiment, the alginate sealing agent of the artificial pleural comprises methacrylated sodium alginate, crosslinked by APS/TEMED or exposure to UV radiation. In certain embodiments, the alginate sealing agent of the artificial pleura comprises both sodium alginate and methacrylated sodium alginate, crosslinked with calcium chloride.

The mechanical properties of the alginate coating of the artificial pleura may be varied to produce an artificial pleura with optimal properties. The mechanical properties of the artificial pleura may be varied, for example, by varying the degree of crosslinking. In one embodiment, the degree of crosslinking is controlled with the concentration of crosslinker (e.g., calcium chloride). In one embodiment the degree of crosslinking is controlled by the degree of methacrylation. In another embodiment, the degree of crosslinking is controlled by the APS/TEMED molar concentration or the UV radiation dosage.

In one aspect, the invention includes a method for sealing a wound in a mammal comprising applying a methacrylated alginate sealing agent to the wound. In some embodiment, the method further comprises exposing the methacrylated alginate sealing agent to a crosslinking agent. When a crosslinking agent is included, it may be calcium chloride; ammonium persulfate (APS) and tetramethylethylenediamine (TEMED), glutaraldehyde, epoxides, oxidized dextran, p-azidobenzoyl hydrazide, N-[α.-maleimidoacetoxy] succinimide ester, p-azidophenyl glyoxal monohydrate, bis-[β-(4-azidosalicylamido)ethyl]disulfide, bis[sulfosuccinimidyl]suberate, dithiobis[succinimidyl proprionate, disuccinimidyl suberate, 1-ethyl-3-P-dimethylaminopropyl]carbodiimide hydrochloride (EDC), N-hydroxysuccinimide (NHS), riboflavin, visible light irradiation, blue light irradiation, ultraviolet irradiation, and combinations thereof.

In one embodiment, methacrylated alginate is formulated in a liquid. When in liquid form, the application of methacrylated alginate may include injecting the methacrylated alginate through a catheter. The catheter may be a fiber optic catheter that is capable of pulsing the methacrylated alginate with visible light. Using a fiber optic catheter such as this would allow crosslinking of the methacrylated alginate to form a hydrogel seal after application to the wound. In such an embodiment, the application further comprises crosslinking the methacrylated alginate.

In another embodiment, the sealing agent or methacrylated alginate is formulated in a solid form, such as powder, film, or other flexible layer form. The solid sealing agent is capable of being hydrated either from fluid at the site of application, such a fluid from surrounding tissues, or exogenous liquid applied to the site. The hydrated sealing agent or methacrylated alginate can be exposed to a crosslinking agent such that the hydrated sealing agent or methacrylated alginate is crosslinked to form a hydrogel seal or patch at the site.

In another aspect, the invention includes a tissue sealant or use of a tissue sealant comprising methacrylated alginate.

Decellularization Kits

In one embodiment, the present invention provides a kit for the production of small decellularized tissue constructs. The kit of the invention comprises all of the reagents necessary to produce one or more small decellularized tissue constructs from an isolated tissue. In one embodiment, the isolated tissue is a whole organ of an animal. The kit comprises reagents for the decellularization of the tissue, the dissection of decellularized tissue sections, the evaluation of decellularized tissue toxicity, and the coating of the decellularized tissue. In one embodiment, the kit comprises instructional material which describes, for example, the formation of decellularized tissue constructs, described elsewhere herein.

In one embodiment, the kit of the invention comprises the reagents required for the decellularization of isolated tissue. Various decellularization methods are well known in the art (Daly et al., 2011, Tissue Engineering Part A, 18: 1-16; Wallis et al., 2012, Tissue Engineering Part C: Methods, 18:420-432; Bonenfant et al, Biomaterials; Sokocevic et al, Biomaterials), and thus the kit of the invention comprises reagents required to carry out one or more of these methods.

For example, in certain embodiments, decellularization of an isolated tissue comprises the application and/or perfusion of one or more solutions to the isolated tissue. Therefore, in one embodiment, the kit of the invention comprises one or more solutions, or reagents necessary to make such solutions, to be applied to the isolated tissue in order to decellularize the tissue. In one embodiment, the reagent or solution comprises an ionic detergent, including but not limited to sodium deoxycholate (SDC), sodium dodecyl sulfate (SDS), Triton X-200, and the like. In one embodiment, the reagent or solution comprises a non-ionic detergent, including but not limited to Triton X-100, Triton X-114, and the like. In one embodiment, the reagent or solution comprises an acidic or a basic solution, including but not limited to paracetic acid. In one embodiment, the reagent or solution comprises a hypotonic or hypertonic solution which lyses cells by osmotic pressure. In one embodiment, the reagent or solution comprises a zwitterionic solution, including but not limited to CHAPS, Sulfobetaine-10 and -16, and the like. In one embodiment, the reagent or solution comprises a solvent, including but not limited to alcohols, acetone, or tributyle phosphate. In one embodiment, the reagent or solution comprises enzymes which degrade cellular components or other biomolecules. In certain embodiments, the reagent or solution comprises an enzyme activating element, such as magnesium or calcium. Such enzymes include but are not limited to trypsin, DNase, RNase, dipase, and the like. In one embodiment, the reagent or solutions may be combined with a physical or mechanical method, including but not limited to freezing and thawing, electrical stimulation, physical force, perfusion, sonication, or agitation.

In one embodiment, the kit of the invention comprises reagents required to assay the presence and/or amount of residual detergent in the decellularized tissue. As described above, decellularization, in certain embodiments, comprises application of one or more detergents to isolated tissue. However, such detergents may be toxic to cells during the recellularization of the decellularized constructs. As such, the kit provides a means for measuring the amount of residual cytotoxic detergents that may remain in the decellularized construct after decellularization. As contemplated herein, the kit may further include any reagents necessary for the further removal of any such trace detergents found to remain on or in the decellularized tissue, such that the decellularized tissue is sufficiently clear of such detergents prior to the application of a sealing agent. In one embodiment, the residual anionic detergents, including but not limited to SDC or SDS, may be detected by determining the amount of methylene blue solubilized in an organic solvent, including but not limited to chloroform. In one embodiment, the residual non-ionic detergents may be detected by determining the amount of luminal signal enhancement in solution. In one embodiment, residual detergents may be removed by additional wash volumes, including but not limited to water or saline solutions.

In one embodiment, the kit of the invention comprises the reagents necessary to coat the decellularized tissue constructs. As described elsewhere herein, a hydrogel coating of decellularized tissue constructs prevents leaking, which therefore allows effective perfusion and ventilation of the constructs. Further, coating of decellularized tissue allows for effective recellularization of the construct. For example, the development of an artificial pleura coating, comprising a crosslinked alginate hydrogel is described elsewhere herein. The kit of the invention comprises reagents required to coat decellularized tissue with the crosslinked alginate hydrogel. In one embodiment, the kit comprises reagents required for the methacrylation of alginate. The reagents of the kit include, but is not limited to, alginate, one or more ammonium salts, DMSO, crosslinking agent (e.g., calcium chloride), water, and the like. As would be understood by those skilled in the art, the kit may comprise any form of alginate, including but not limited to high molecular weight (200,000 Da) and low molecular weight (50,000 Da) alginate. In some embodiments, the reagents may be applied to the decellularized tissue as a single solution. In other embodiments, the coating reagents may be provided and applied to the decellularized tissue as two solutions. For example, the first solution may include the alginate or methacrylated alginate, and may be applied to the decellularized tissue. Then, the second solution, containing the crosslinking agent such as calcium chloride, may be applied to crosslink the previously applied first solution.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

The Materials and Methods used in the performance of the experiments disclosed herein are now described.

Decellularization of Human Lungs:

Cadaveric human lung lobes were obtained from autopsy services at Fletcher Allen Hospital in Burlington, Vt. Lungs were categorized as normal or diseased based on review of available clinical records, including known history of lung disease, smoking history, chest radiographs, and use of respiratory medications. No other patient-specific identifiers were utilized. Whole lungs or individual lobes were decellularized using a previously optimized method for lungs from large animals or humans based on modifications from approaches utilized in mouse lungs. In brief, lungs were exposed to sequential washes of Triton X-100, sodium deoxycholate (SDC), 1 M NaCl, and DNAse, with intermittent washes with deionized (DI) water and extensive rinsing with phosphate-buffered saline (PBS).

Viscosity Measurements of Sodium Alginate (Na-AA):

Solutions of high molecular weight Na-AA (Manugel®, FMC Biopolymer, Philadelphia, Pa.) or low molecular weight Na-AA (Protanol_, FMC Biopolymer, Philadelphia, Pa.) were made at concentrations ranging from 0.5 to 5% (w/v) in deionized water. Solution viscosities were determined using a rheometer (AR2000, TA Instruments, New Castle, Del.). Utilizing a 40 mm-diameter, 1_ angled cone geometry, alginate solutions (0.5-2% (w/v)) were exposed to varying degrees of shear (1-140/s) at 1% radial shear strain.

Synthesis of Calcium Alginate Hydrogels:

Ionically crosslinked hydrogels were synthesized using varying concentrations of calcium chloride ($CaCl_2$, 2-10% (w/v)) (Supplementary FIG. 1). Wet mass, as an indication of extent of crosslinking, was determined for different combinations of Manugel® and $CaCl_2$ solutions. With the exception of the viscosity measurements, all subsequent references to Na-AA refer to Manugel® formulation.

Mass Swell Ratio Determination:

The mass swelling ratio ($Q_{mass}$) was determined by dividing the wet by dry mass of calcium alginate hydrogels synthesized with different initial concentrations of Na-AA. Following ionic crosslinking with 3% (w/v) $CaCl_2$, all calcium alginate (Ca-AA) hydrogels were dried overnight in a desiccator to determine dry weight.

Degradation of Calcium Alginate:

200 IL of alginate solution at 2.5, 3, 4, and 5% (w/v) were ionically crosslinked with 200 IL of 4 or 10% (w/v) $CaCl_2$ in a 48 well cell culture plate. Calcium alginate hydrogels were allowed to form and the excess liquid was aspirated off. Initial wet weights were taken for each hydrogel and taken at days 7 and 14. Degradation experiments were carried out in 0.05% (w/v) sodium azide in 19 PBS in a humidified incubator at 37° C. and 5% $CO2$.

Synthesis of Methacrylated Alginate (AA-MA):

Methacrylation of Manugel_ was performed using an aqueous reaction with methacrylic anhydride. Briefly, a 2% (w/v) polymer solution was reacted with a 20 molar excess of methacrylic anhydride for 24 h at room temperature, adjusting pH to approximately periodically with sodium hydroxide. The polymer was then precipitated with cold ethanol, re-hydrolyzed and dialyzed against deionized water extensively.

Photocrosslinking of Methacrylated Alginate:

Methacrylated alginate was dissolved in deionized water to make 2 or 3% (w/v) solutions with 0.00125% (w/v) eosin Y (photosensitizer), 125 mM triethanolamine (TEOA, initiator), and 19 mM 1-vinyl-2-pyrrolidinone (1VP, catalyst) and exposed to 530 nm green light using a custom light set-up comprised of four green LEDs soldered to 10 mm2 CoolBase (SR-05-M0070, Luxeon Star LEDs, LEDDynamics, Ontario, Canada) and mounted on a 40 mm2 9 10 mm Alpha Heat Sink (LPD40-10B, Luxeon Star LEDs, Ontario, Canada) The whole assembly is powered by 9 V DC. Photocrosslinked methacrylated alginate was made by injecting 2-3% (w/v) AA-MA solutions with eosin Y, TEOA, and 1VP between two glass coverslips and exposing to 530 nm light for 10 min. Discs of uniform size were then generated using a 6 mm biopsy punch.

Mechanical Characterization of Sodium and Methacrylated Alginate:

One mL of a 3% (w/v) methacrylated alginate solution containing photoinitiator was placed between two parallel plates on an AR2000 Rheometer (TA Instruments) at room temperature (n=3). Viscosity (PaÆs) of the solution was collected under 1% radial strain at strain rates between 1 and 140 per second over the course of 3 min Following viscosity data collection, a green light system (520 nm) custom for rheometry collection was activated while collecting loss and storage moduli, and delta (the phase angle between the moduli) at 1% radial strain and 1 Hz over the course of 20 min. Gelation, or initiation of hydrogel photocrosslinking, was determined as the inflection point on the delta curve.

Ionic or Photocrosslinking on Excised Segments of Acellular Lung:

2.5% (w/v) alginate or 2-3% (w/v) AA-MA was applied to the excised lung segments and allowed to equilibrate prior to either ionic or photo-initiated crosslinking Ionic crosslinking was achieved by exposing alginate coated acellular lung segments to a 3% (w/v) CaCl2 solution. AA-MA was covalently crosslinked by exposing coated acellular segments to 530 nm wavelengths in a custom made light box with four green LEDs. The ability of excised segments of acellular lungs coated with calcium alginate hydrogels to retain injected solutions was assessed by instilling Trypan blue solution through a cannulated small airway.

Cell Culture and Cellular Inoculations:

Human lung epithelial carcinoma cells, A549 (ATCC) were cultured in DMEM/F12 basal medium supplemented with 10% fetal bovine serum, 1% penicillin-streptomycin, and 1% L-glutamine. Human bronchiolar epithelial cells, HBEs (courtesy of Albert van der Vliet, University of Vermont, originally from Drs. J. Yankaskas and R. Wu) were cultured in DMEM/F12 basal medium supplemented with cholera toxin (10 ng/mL), epidermal growth factor (10 ng/mL), insulin (5 lg/mL), transferrin (5 lg/mL), dexamethasone (0.1 lM), bovine pituitary extract (15 lg/mL), bovine serum albumin (0.5 mg/mL), and 1% penicillin-streptomycin. Human endothelial progenitor cell line, CBF (courtesy of Mervin Yoder (IUPUI)) were cultured on collagen coated tissue culture plastic in EGM-2 complete medium (Lonza) supplemented with 10% fetal bovine serum and 1% penicillin-streptomycin. Human lung fibroblasts were cultured in DMEMbasal medium supplemented with 10% fetal bovine serum, 1% penicillin-streptomycin, 1% L-glutamine. All cell lines were cultured at 37° C. and 5% CO2. Cells were seeded and cultured at specified confluence and passaged and maintained accordingly. For all cell seedings, cells were washed with PBS 39, lifted with TrypLE Express (Life Technologies), washed with FBS containing medium and re-suspended at the appropriate concentration in their respective complete medium.

For recellularization studies, endothelial cells were seeded into vascular spaces of excised acellular human lung segments through cannulated small vessels and epithelial cells were seeded through cannulated small airways. The excised segments were either coated with calcium alginate hydrogels or left uncoated. Inoculation efficiency was assessed by seeding approximately same sized segments which had either been coated with calcium alginate hydrogels or left as excised with 2 9 106 HLFs. Cells which had leaked out of the segments were counted using a hemocytometer. For long term culture studies, calcium alginate coated segments were seeded with either HBEs, or CBFs through cannulated small airways or vessels, respectively. Cells were allowed to adhere and then the segments were sliced into 2-3 mm thick slices and cultured for 28 days. Slices were harvested at 1, 3, 7, 14, 21, and 28 days.

Cytotoxicity of Degradation Products:

HLFs were seeded at 10,000 cells/well in 48 well tissue culture plates and allowed to adhere for 24 h. Cytotoxic effects of degradation products were evaluated by incubating Ca-AA or AA-MA hydrogels made from a 6 mm biopsy punch in 500 IL of HLF complete media for 24 h. The supernatants were collected and applied to HLFs and incubated an additional 24 h. Cytotoxicity was assessed using Cytotox96 (Promega) according to the manufacturer's direction. HLFs cultured on tissue culture plastic in complete media were used as a control. Maximum LDH release was assessed in HLFs similarly cultured for 48 h and completely lysed with 9% Triton X-100.

Mechanical Ventilation of Methacrylated Alginate Coated Segments:

Segments coated with methacrylated alginate were mechanically ventilated (HugoSachs MiniVent Type 845, Harvard Apparatus, Holliston, Mass.) at 200-300 IL tidal volumes, 1-3 Hz frequency, and 2 cm H2O positive end expiratory pressure (PEEP). Mechanical stability of the coating and the ability of the segment to be inflated without rupturing the pleural coating were evaluated by visual inspection. Retention of air in the segments was confirmed by the presence of air escaping through the PEEP trap.

Lung Histology:

Acellular human lung segments, segments coated with calcium alginate or photocrosslinked methacrylated alginate, and recellularized slices of acellular tissue were fixed for 10 min in 4% paraformaldehyde at room temperature. After embedding in paraffin, 5 lm tissue sections were mounted on glass slides. Following deparaffinization, sections were stained with hematoxylin & eosin (H&E) and assessed by standard light microscopy. All light microscopy images were taken with an EVOS™ Digital Color Fluorescence Microscope (Advanced Microscope Group, Bothell, Wash.).

Statistics:

Differences in initial wet mass were determined using two-way ANOVA, with Tukey's multiple comparison's test. Multiplicity p-values are reported for each comparison. Cytotoxicity (LDH) analysis of degradation products and differences between qmass was performed using one-way ANOVA. All cytotoxicity data are represented as percent of maximum LDH release control (cells cultured in tissue culture plastic for 48 h and lysed with 9% Triton X-100) ±standard deviation. Cytotoxicity and qmass data are presented as mean±standard deviation. Post-analysis multiple comparisons were conducted using the Tukey test with a 95% confidence level and p<0.05 considered statistically significant. Cell retention data was analyzed using Student's t test. All statistical analyses were performed using Graph-Pad Prism 6.

The Results of the experiments disclosed herein are now described.

Example 1

Methacrylation of Alginate

Methacrylation of alginate (AA-MA) was achieved by complexing alginate with an ammonium salt and performing the reaction in dimethyl sulfoxide (DMSO) with the desired molar ratio of methacrylic anhydride; the polymer was then hydrolyzed with sodium chloride to return the bio-molecule to its native, hydrophilic state. The methacrylation of alginate in DMSO was found to increase the efficiency of the methacrylation reaction and to permit control of the degree of methacrylation; the molar ratios between the methacrylic anhydride and alginate hydroxyl groups were 1:1, 1:2, and 1:4, respectively. The degree of modification was characterized by $^1$H-NMR and determined by integrating the methacrylate proton peaks (methylene, $\delta$=6.0 and 5.6 ppm and the methyl peak, $\delta$=1.8 ppm) and comparing to carbohydrate protons to determine molar percent of methacrylation. A degree of modification of up to 80% was achieved with high fidelity (FIG. 1A). The cytotoxicity of AA-MA hydrogels was also evaluated. AA-MA hydrogel films were cast into 24-well tissue culture polystyrene plates; the AA-MA films were either ionically crosslinked with $CaCl_2$ solution or covalently crosslinked Murine macrophage cells (RAW 264.7) were seeded at a density of 100,000 cells/well in 1 mL complete medium on top of the hydrogel films and incubated at 37° C. and 5% $CO_2$ for 24 hours. Cell viability was determined to be greater than 95% using a MTT-based assay.

Figure 1B:
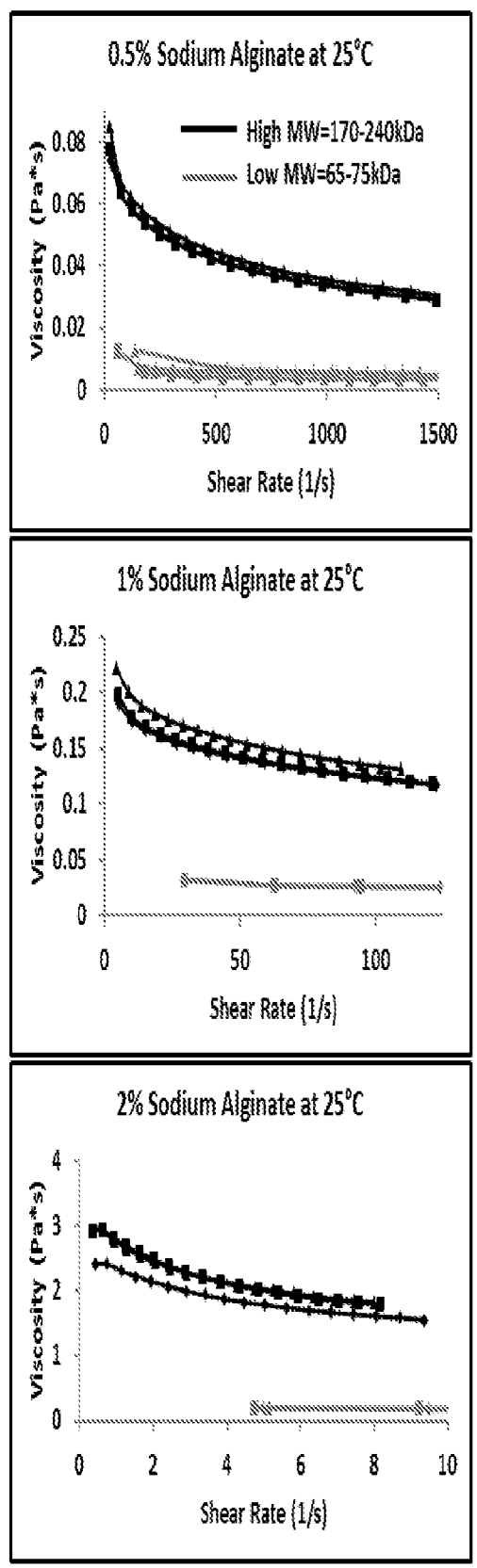
FIG. 1B depicts the production of methacrylated sodium alginate and the viscosity of sodium alginate solution. Increased molecular weight and concentration (w/v) increase the solution viscosity of sodium alginate at 25° C.

The viscosity of alginate solution can be precisely controlled by varying the molecular weight of the polymer and the concentration of the solution. Increasing the molecular weight of the polymer while maintaining the concentration (w/v) results in an increase in viscosity at 25° C. (FIG. 1B). (For comparison, the viscosity of water is 0.001 Pa·s, honey-10 Pa·s, and vetbond surgical glue is 4.3 Pa·s.). Having control over the initial solution viscosity is imperative for precise application of the alginate or AA-MA solution. Viscosities which are too low will prevent the formation of an initial continuous coating with suitable mechanical stability for subsequent crosslinking Viscosities which are too high will prevent the solution from being applied evenly. Therefore, it is important to have the ability to synthesize solutions with a variety of viscosities to choose an optimal composition, depending on the target application. The mechanical properties of the crosslinked alginate coating can then be controlled by varying the degree of crosslinking, which will be controlled with calcium chloride concentration, degree of methacrylation, and/or UV radiation dosage.

Figure 2:
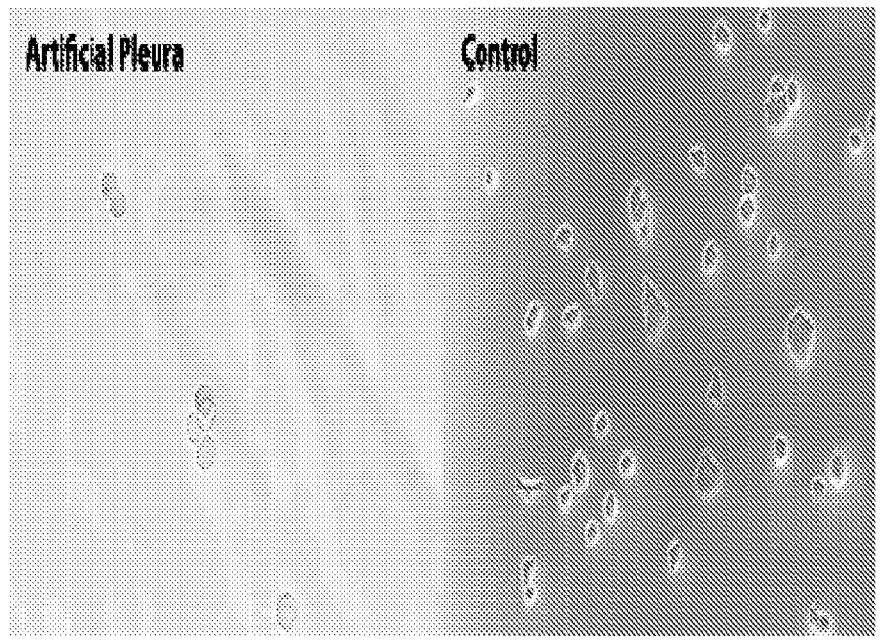
FIG. 2 is a set of images depicting the results of experiments demonstrating that the artificial pleura prevents cellular adhesion of a test cell type (A549 lung carcinoma cells) after 4 hours. The A549 cells can be seen to be attaching to the tissue culture dishes and adopting an adherent phenotype while those cells seeded on the artificial pleura remain spherical and are not adherent. Original mag=200×.

As contemplated herein, the cells inoculated into the coated de-cellularized lungs should attach primarily to the tissue extracellular matrix scaffold and not the alginate coating (i.e. artificial pleura). It was found that the artificial pleura (coating) prevents cellular adhesion of a test cell type, A549 lung cancer cells (FIG. 2). The cells can be seen to be attaching to the tissue culture dishes (control) and adopting an adherent phenotype while those cells seeded on the artificial pleura remain spherical and are not adherent after 4 hours.

Example 2

Decellularized Human Lung Segments Coated with Alginate

Figure 3:
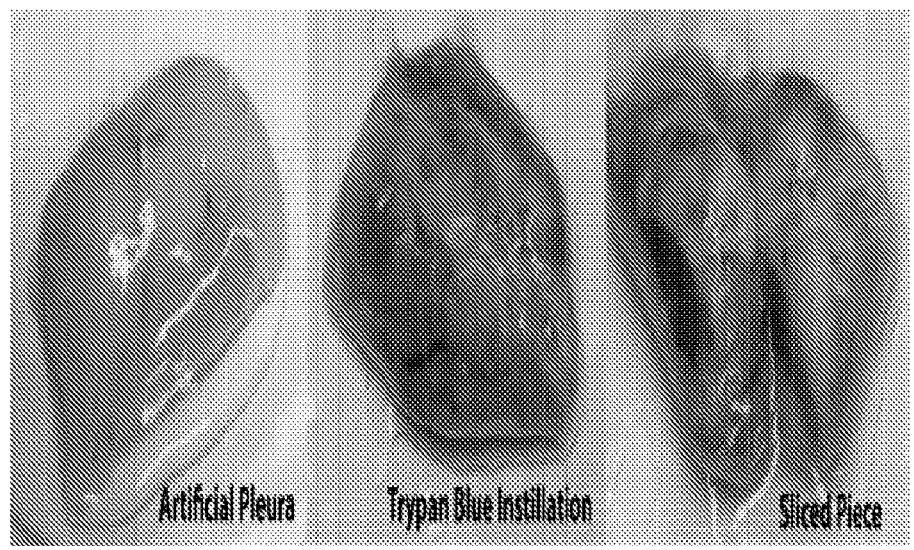
FIG. 3 is a set of images depicting a human lung segment after inflation with a Trypan blue-containing saline, which demonstrates the ability of the artificial pleura to maintain airway and vasculature integrity and mechanical stability for inflation.
Figure 4:
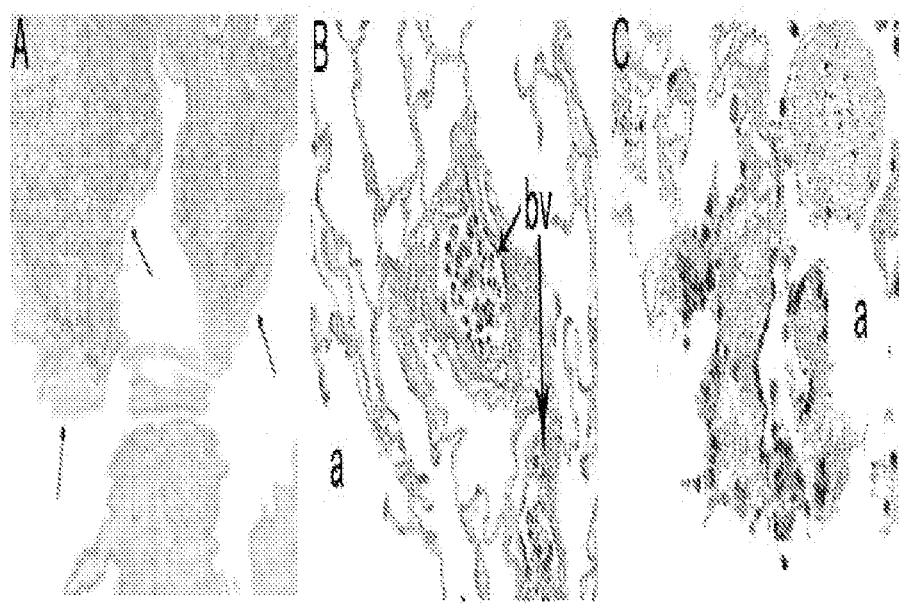
FIG. 4, comprising
Figure 5:
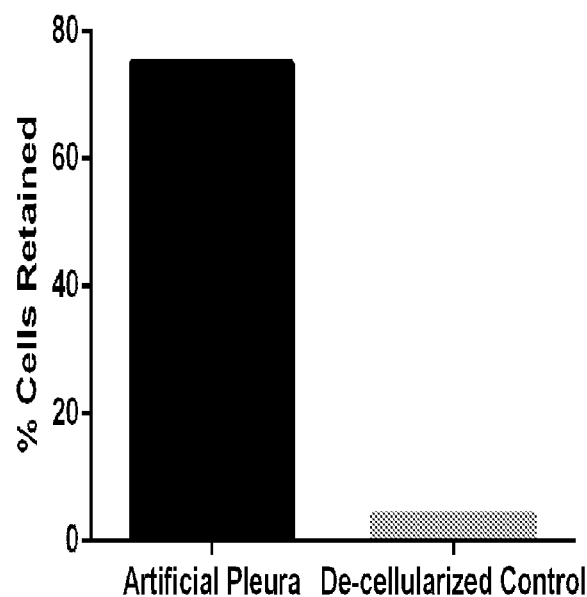
FIG. 5A is a graph depicting the results of experiments demonstrating that application of an artificial alginate pleura enhances cellular retention in human lung segments. Human decellularized lung segments retain up to 75% A549 cells with artificial alginate pleura as compared to 5% retention with decellularized lung (no coating, control).

It is demonstrated herein that calcium alginate is a powerful tool allowing for an intact coating of tissue that prevents leak, allows ventilation (stretch), and supports retention and robust growth of inoculated cells (FIGS. 3-5).

Normal and emphysematous human lungs were obtained from the autopsy service at Fletcher Allen Hospital in Burlington, Vt. These lungs were decellularized using a previously published protocol of intratracheal and vascular perfusion using sequential incubations with Triton X-100, sodium deoxycholate, sodium chloride, and DNase (Daly et al., 2012, Tissue Engineering Part A, 18: 1-1; Wallis et al., 2012, Tissue Engineering Part C: Methods, 18:420-432; Bonenfant et al, Biomaterials, 2013; Sokocevic et al, Biomaterials, 2013). Pieces of de-cellularized lungs were then coated with a 2.5% sodium alginate solution or left uncovered. The artificial pleura consisted of a calcium alginate hydrogel (Umeda 2009, Acta Oto Laryngologica, 129: 1509-1518) generated by crosslinking the sodium alginate-covered lung pieces with 3% calcium chloride solution. Segments were then inoculated through the airways with either human lung fibroblasts, or through the vasculature with endothelial progenitor cells and then statically cultured and harvested at various time points. Presence of the artificial pleura, cell engraftment and survival were assessed by histochemical and immunohistochemical staining. In vitro anti-adhesion assays were performed using human alveolar carcinoma cells (A549s). The integrity of the artificial pleura and its ability to be inflated was assessed through instillation of Trypan-blue through both the vasculature and airway branches in each piece.

The lungs pieces were able to be fully inflated and retained the Trypan blue without rupture of the artificial pleura (FIG. 3). The artificial pleura was found to be intact and lining the periphery of the decellularized matrix by histological inspection (FIG. 4). Decellularized human lung segments which had been encased in the artificial pleura were found to retain up to 75% of the inoculated cells while those segments devoid of pleura only retained about 5% (FIG. 5). A549s did not adhere to the artificial pleura material during the in vitro anti-adhesion assay. Importantly, in parallel with coating de-cellularized lung segments, the alginate coating can also be applied in discrete spots to cover or plug individual leaks in the de-cellularized lungs (data not shown). Thus the alginate coating has two highly practical uses in the study of lung decellularization and recellularization.

Example 3

Synthesis of Alginate Coatings with Varying Elastic Moduli and Determination of a Method for Producing a Mechanically Controllable Pleural Coating The studies presented herein examined the synthesis of alginate gels with various elastic moduli by varying the extent of crosslinking. The concentration of initial alginate (AA) or methacrylated alginate (AA-MA) (low and high molecular weight) and extent of ionic and/or covalent crosslinking are systematically varied to generate initial solutions with different viscosities and final crosslinked gels with varying elastic moduli.

Figure 6A:
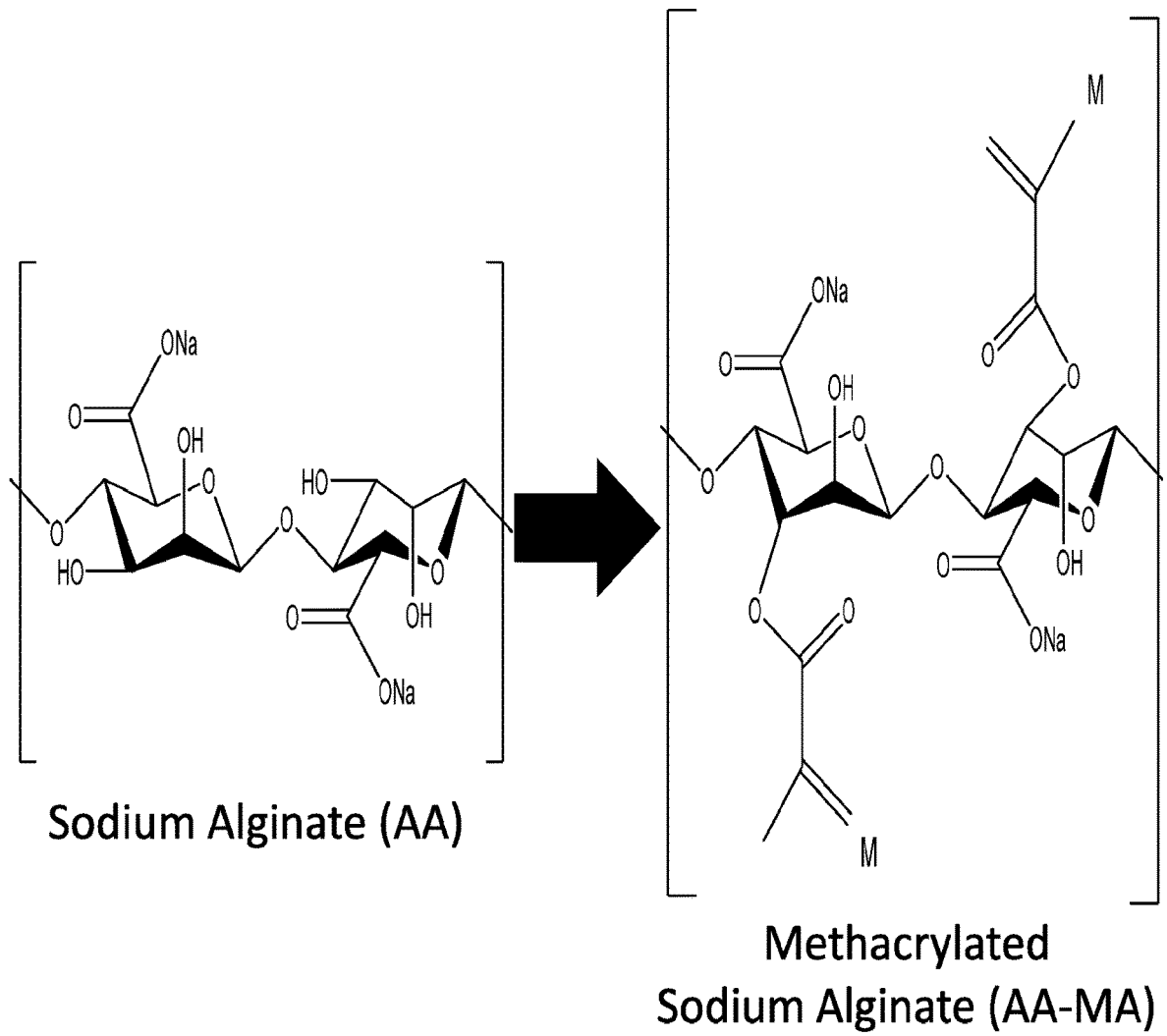
FIG. 6A is a schematic depicting the methacrylation of sodium alginate.
Figure 6B:
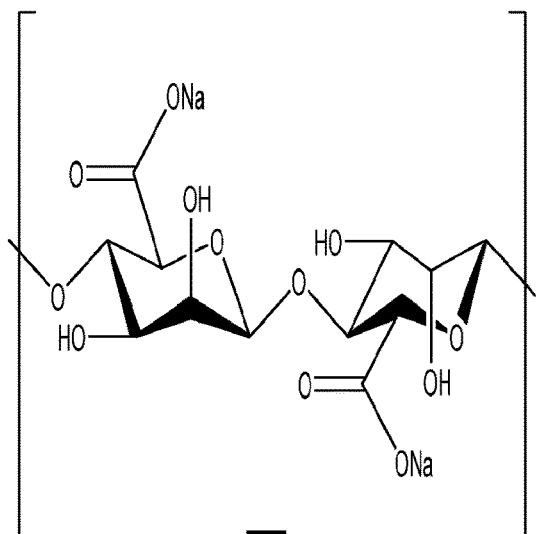
FIG. 6B is a schematic depicting the methacrylation and the method of calcium cross-linking alginate.
Figure 6B:
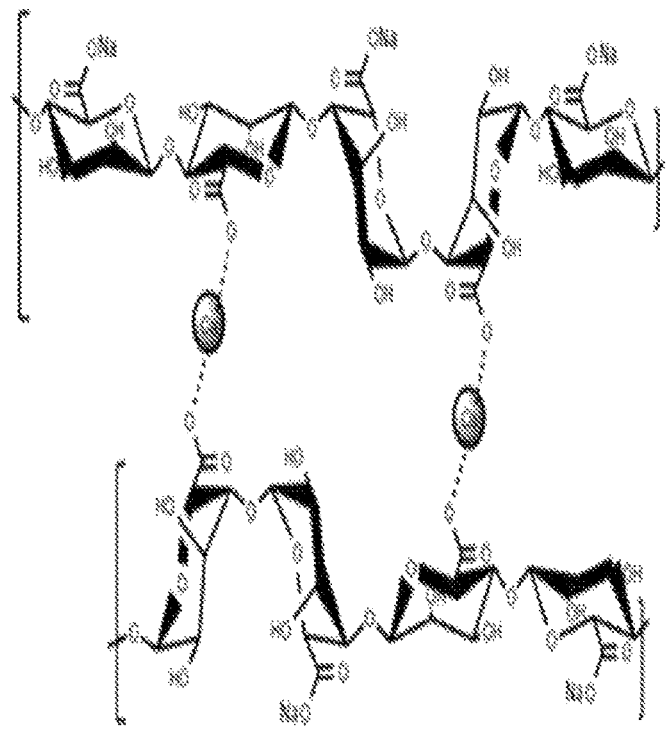
Figure 6C:
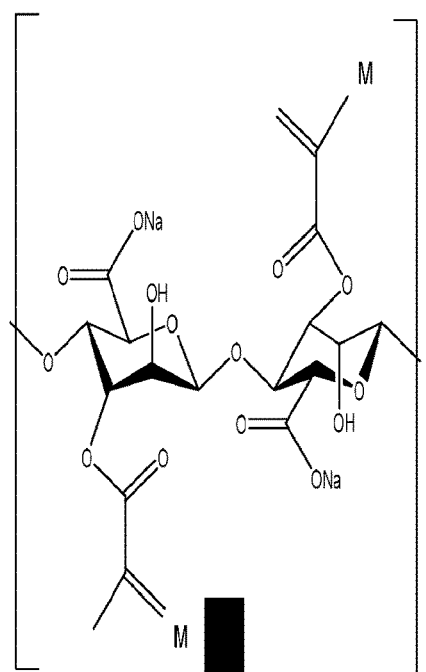
FIG. 6C is a schematic depicting the methacrylation and the method of UV cross-linking alginate.
Figure 6C:
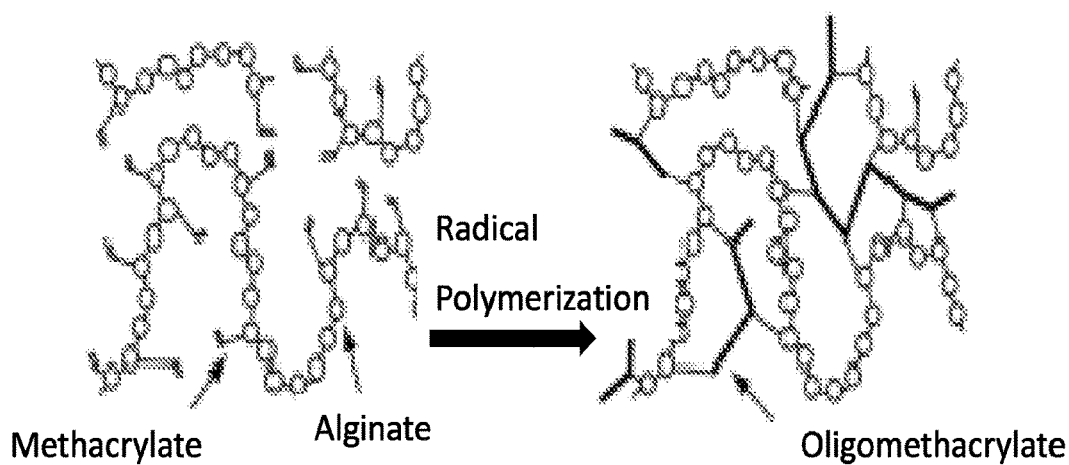

FIG. 6 depicts an exemplary schematic demonstrating the methacrylation of alginate (FIG. 6A) and various methods of cross-linking alginate (FIG. 6B) and methacrylated alginate (FIG. 6C).

A 1% (w/v) hexadecyltrimethylammonium bromide (CTAB) solution is added to a 1% (w/v) alginate solution and mixed at room temperature for 24 h; the molar ratio of COOH:CTAB is 1:1. The precipitate AA-CTAB is lyophilized and dissolved in anhydrous DMSO to form a 0.5% (w/v) solution. Next, methacrylic anhydride is added to the solution and mixed at room temperature overnight. The volume of methacrylic anhydride is varied to synthesize polymers with different degrees of modification; the molar ratios between the methacrylic anhydride and alginate hydroxyl groups is 1:1, 1:2, and 1:4, respectively. The degree of methacrylation is assessed using $^1$H-NMR by integrating the methacrylate proton peaks (methylene, $\delta$=6.0 and 5.6 ppm and the methyl peak, $\delta$=1.8 ppm) and comparing to carbohydrate protons. The impact of crosslinking on the underlying decellularized scaffold architecture is assessed using histology following application of AA or AA-MA solutions following differential crosslinking.

Experiments are also performed to determine if the method of crosslinking impacts the underlying decellularized lung tissue. AA is ionically crosslinked via calcium chloride solution application and AA-MA is covalently crosslinked via UV radiation.

Solution viscosities of 0.5, 1, 2, 3, 4, and 5% solutions (w/v) of high (200,000 Da) and low (50,000 Da) molecular weight AA and AA-MA is assessed using a rheometer (ARES 2000, TA Instruments) at both 25° C. and 37° C. AA and AA-MA solutions of varying concentrations are cast in 6 well plates and the degree of crosslinking is varied using 0.5, 1, 2, 3, 4, and 5% (w/v) $CaCl_2$ solutions or UV irradiation dosing. Mechanical properties (i.e. elastic modulus and ultimate strength) of each crosslinked material are derived from uniaxial unconfined compression on the rheometer and analyzed offline using a custom program.

Further, the degradation rate of alginate coatings are characterized. Integrity of the crosslinked alginates are assessed in the presence of aqueous solutions containing calcium chelators and enzyme solutions.

Polymers degrade in one of three predominant modes: hydrolytic, enzymatic, or mechanical degradation. Therefore, the contribution of each mode of degradation is assessed in the alginate pleura system. While some pathogens produce alginases, it is not anticipated that alginate-specific enzymatic degradation to be a dominant mode of degradation in the artificial pleura system approach. Therefore, the rate of "enzymatic degradation" is assessed using complete cell media to assess non-specific enzymatic degradation. The extent of degradation in the different materials is assessed using the following approaches: (a) Hydrolytic degradation in PBS supplemented with tris-EDTA is monitored over 28 days. Each sample is weighed prior to being immersed in PBS and placed in a shaker-incubator at 37° C. At 1, 3, 7, 14, 21, and 28 days, the material is removed from the wells, lyophilized and weighed. The materials are then returned to their respective wells with fresh PBS and stored at 37° C. until the next time point (n=6). (b) Enzymatic degradation in complete cell media (DMEM F-12, 10% FBS, 1% Penicillin/Streptomycin, 1% L-glutamine) at 37° C. for 1, 3, 7, 14, 21, and 28 days (c) Mechanical degradation in complete media is assessed by casting and crosslinking gels into uncoated FlexCell 6 well plates (FlexCell Int. North Carolina) and stretched biaxially at 5%, 1 Hz for 1, 3, and 5 days.

Example 4

The Utility and Effectiveness of Alginate-Coated Lung Segments for Study of Recellularization and Development of Functional Human Lung Tissue Described herein are studies examining whether crosslinked alginate can be utilized as an effective artificial pleura and provide sufficient mechanical integrity and strength for lung segments to be ventilated. The mechanical integrity of crosslinked alginate formulations with suitable elastic moduli on a 3-dimensional de-cellularized lung segments is assessed using FlexiVent. The degree of inflation of each segment (i.e. extent of mechanical integrity and strength) is assessed by comparing pre- and post-coating resistance curves on the same segments.

Figure 7:
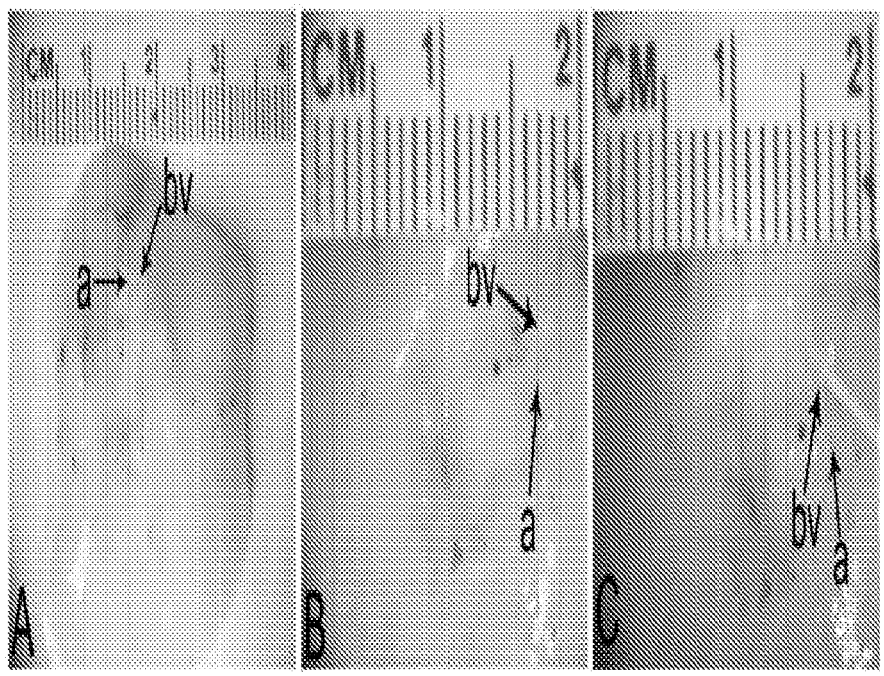
FIG. 7 is a set of images depicting an exemplary decellularized human lung segment. a=airway, bv=blood vessel.

Human lungs are decellularized by sequential treatment with distilled water, Triton-X, sodium de-oxycholate, and porcine pancreatic DNAse (Sigma) as established in previously reported protocols (Daly et al., 2012, Tissue Engineering Part A, 18: 1-16; Wallis et al., 2012, Tissue Engineering Part C: Methods, 18:420-432; Bonenfant et al, 2013, Biomaterials; Sokocevic et al, 2013, Biomaterials). Following decellularization, small regions, for example regions having a volume of about 1-3 $cm^3$, of the lung are dissected out using a dissecting microscope, each segment having easily identifiable bronchovascular bundles (airway, pulmonary artery, pulmonary vein) (FIG. 7).

As there is no means of determining appropriate ventilation parameters a priori for small lung segments, a range of tidal volumes and frequencies are initially empirically assessed using a HugoSachs minivent on non-recellularized lung segments coated with the varying alginate formulations. Segments are used with approximately the same size and from comparable regions in the lung. Comparisons are with ventilation of intact (ie non-decellularized) human lung lobes.

Further experiments are performed examining if culture of decellularized human lung segments using different alginate coatings support initial binding and subsequent viability, proliferation and differentiation of inoculated cells. A systematic combinatorial approach is utilized to assess different epithelial, endothelial, and parenchymal populations.

Three different representative human lung origin cell types are inoculated into the different alginate-coated decellularized lung chunks: a) human bronchial epithelial (HBE) cells; b) human pulmonary vascular endothelial cells (CRF 041312 cells; and c) human lung fibroblasts (ATCC). For each of the cell combinations indicated above, $1 \times 10^6$ cells of each cell type are administered by airway or vascular inoculation into the differently coated lung segments. Segments are submerged in basal media at 37° C. overnight to allow initial cell adherence. The segments are then cultured under static conditions or ventilated and perfused (Custom bioreactor set up with a HugoSachs minivent and a custom benchtop perfusion system) for 1, 3, 7, 14, or 28 days. Optimal ventilation parameters are utilized as determined above. Optimal perfusion parameters are applied as determined from parallel ongoing experiments. Endpoints include efficiency of seedings and localization, proliferation, and differentiation of inoculated cell types. Controls also include decellularized lung segments coated with non-cross-linked alginates.

Lung segments are assessed for lung mechanics using the forced oscillation technique (Flexivent; Gomes et al., 2001, J. Appl Physiol, 90(5): 1631-1638). A section of each segment is removed for quantitative RT-PCR assessment expression of characteristic markers for the inoculated cell types including CC10, CFTR, β-tubulin, ZO-1, E-cadherin, AQP-5, SPC, CGRP, TTF-1 (Nkx2.1), CD31, Tie-2, Col-1, and αSMA The remaining portion of the segment is then gravity fixed (20 cm $H_2O$) with 4% paraformaldehyde for 1 hr at room temperature and subsequently assessed for initial binding and subsequent proliferation of lung epithelial, interstitial, and pulmonary vascular cells and for airway and alveolar-like structure by light and confocal microscopy to assess three-dimensional cell architecture (Hematoxylin and Eosin-stained 5 µm paraffin-sections) and by immunohistochemical evaluation for positive qRT-PCR markers of specific cell types, as described above, and for characteristic ECM proteins including types I and IV collagens, fibronectin, laminin, and elastin. Cell proliferation and apoptosis are assessed by Ki67 and caspase-3 staining, respectively. Cells exhibiting staining patterns of specific epithelial, interstitial, or vascular phenotypes are counted on serial sections and normalized for the total number of cells counted.

Example 5

Methacrylated Alginate Hydrogel Sealant to Repair Pleural Leaks

The use of methacrylated alginate to overcome the limitations of the current approaches has not been previously evaluated or utilized as an artificial pleural coating in any context. A novel approach was developed to provide an easy-to-apply hydrogel sealant which can rapidly repair pleural leaks. This involves use of a modified form of alginate, a naturally occurring seaweed derivative, increasingly being explored for repair of a variety of other tissues. Particular attributes include easy availability, low cost, easy use, and lack of significant toxicity.

Figure 8:
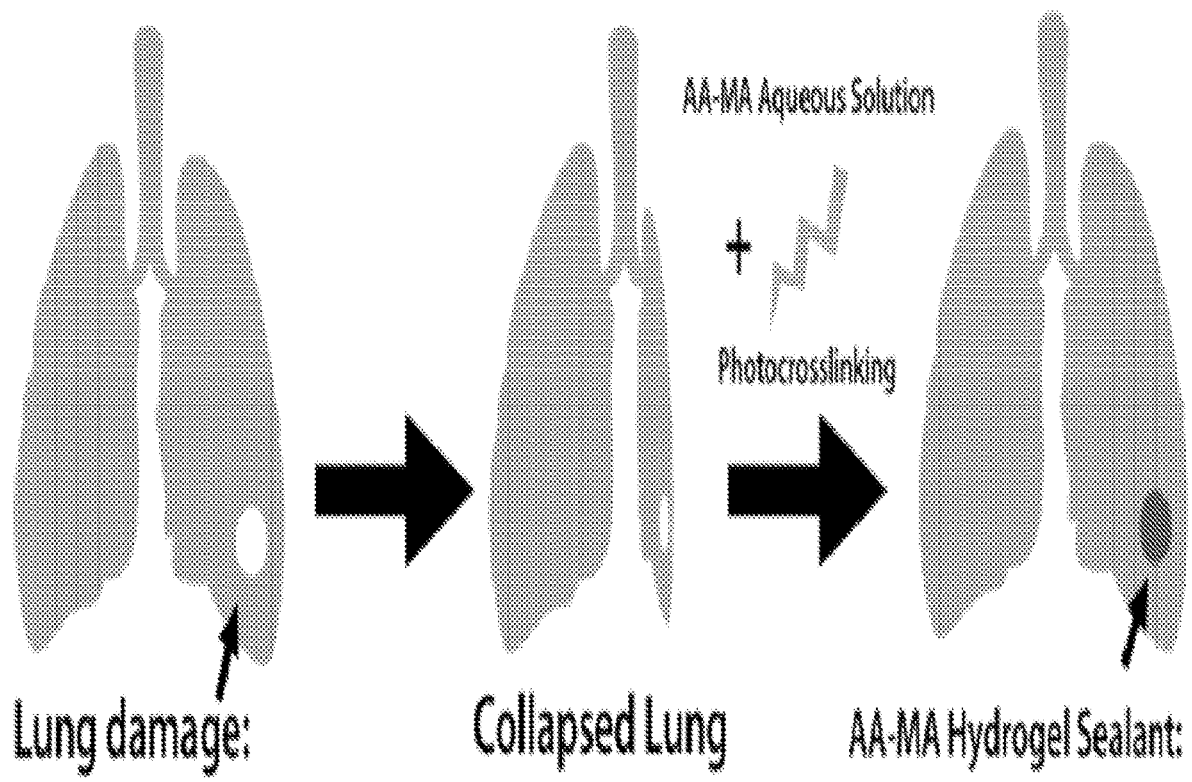
FIG. 8 is a schematic diagram showing methacrylated alginate (AA-MA) can be applied as an aqueous solution with controlled viscosity and photocrosslinked to seal damaged lungs and permit reinflation.

Sodium alginate can be applied in a liquid or patch form and can then be cross-linked to form a hydrogel that produces a physical seal. Further, chemical modification of alginate (eg. addition of methacrylate groups for covalent crosslinking) has been studied extensively for optimizing physical and mechanical properties and thus, broadening its use into new clinical applications. As such, a novel approach was developed that utilizes methacrylated alginate which can be cross-linked using appropriate photosensitizers and photoinitiators by brief exposure to visible light (photopolymerization/photocrosslinking) to form a non-toxic, flexible pleural seal that provides tensile strength and durability, ideal for pulmonary applications such as repairing bronchopleural fistulas or in clinical scenarios where pleurodesis is unsuccessful such as malignant pleural effusions (FIG. 8).

Figure 9:
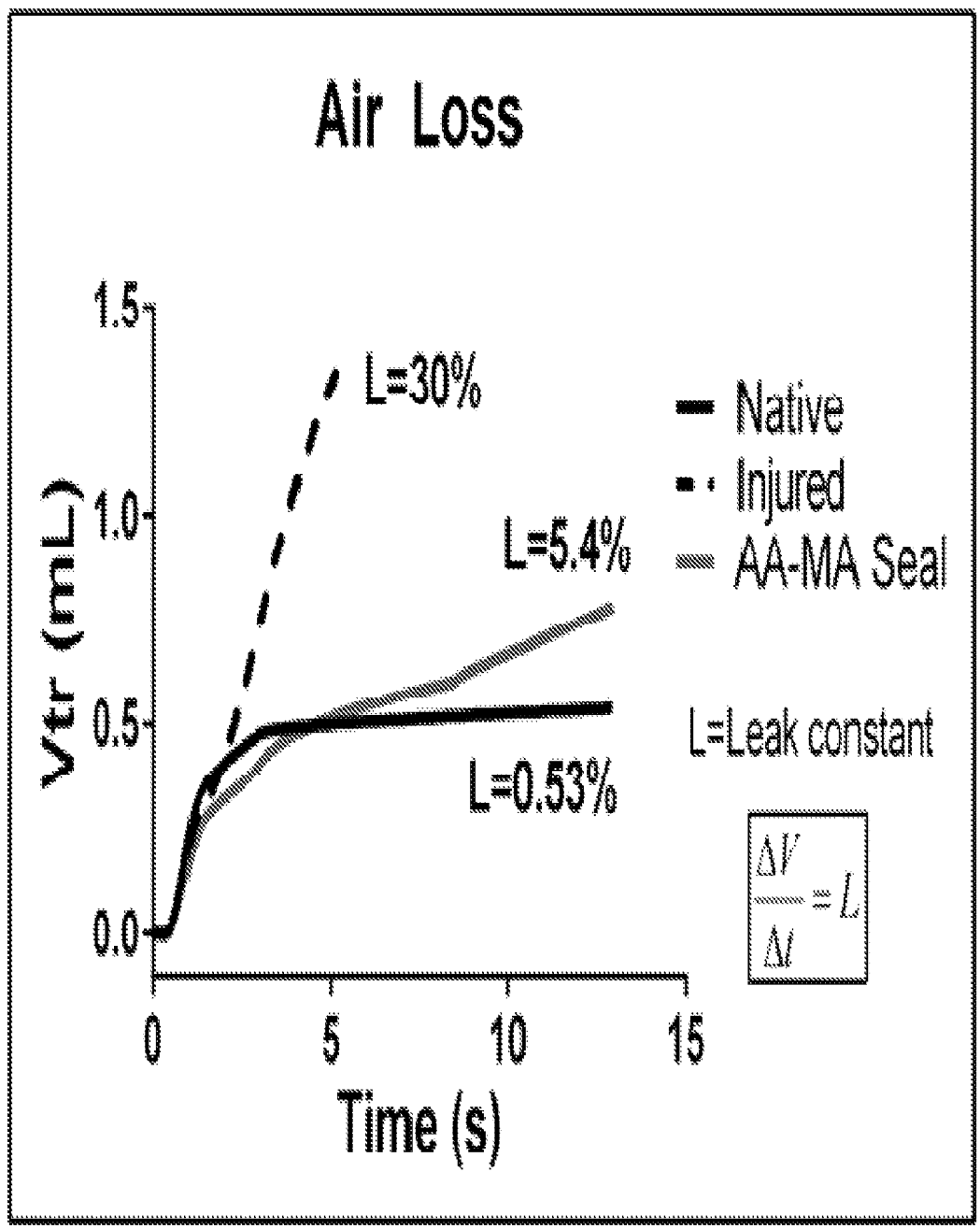
FIG. 9 is a graph showing photocrosslinked methacrylated alginate repaired experimental injury and restores gas volume in excised mouse lungs. Representative example demonstrates that re-inflation occurred with constant pressure following repair of an experimental lung injury with photocrosslinked AA-MA.

Photocrosslinked methacrylated alginate has been found to be an effective approach for repairing experimentally induced leaks in mouse lungs (FIG. 9). FIG. 9 is a representative example demonstrating that photo-crosslinked methacrylated alginate repaired experimental injury and restored gas volume or re-inflation with constant pressure in excised mouse lungs.

The methacrylated alginate will be utilized in one of two ways: a) application in either liquid or patch form during surgery (thoracotomy) with subsequent photocrosslinking by brief exposure to visible light; b) application of a liquid injected through a visually-directed fiber-optic catheter that has capacity to then pulse with visible light for photocrosslinking. This procedure is akin to commonly utilized video-assisted thoracic surgery (VATS) and medical pleuroscopy approaches performed by thoracic and trauma surgeons as well as medical intensivists. Notably the video-assisted approach is amenable for battlefield and other trauma situations and can serve as a temporary life-saving maneuver until more definitive operating room approaches are available.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of recellularizing a decellularized lung tissue, comprising the steps of:
   decellularizing an isolated lung tissue sample to form a decellularized lung tissue, wherein the isolated lung tissue sample is a whole organ or a portion thereof;
   applying a first coating to at least a portion of the decellularized lung tissue, wherein the first coating comprises a hydrogel sealing agent comprising a hydrogel solution comprising alginate;
   applying a second coating to the portion of tissue, wherein the second coating comprises one or more crosslinking agents that crosslink the alginate coated on the decellularized lung tissue; and
   contacting the decellularized lung tissue with at least one cell type;
   wherein the hydrogel sealing agent coating prevents leakage of liquids and gases from the decellularized isolated tissue sample.

2. The method of claim 1, wherein the alginate is crosslinked by exposing the hydrogel sealing agent to at least one crosslinking agent selected from:
   one or more compounds selected from the group consisting of eosin Y, triethanolamine, calcium chloride; ammonium persulfate (APS) and tetramethylethylenediamine (TEMED), glutaraldehyde, an epoxide, oxidized dextran, p-azidobenzoyl hydrazide, N-[α.-maleimidoacetoxy]succinimide ester, p-azidophenyl glyoxal monohydrate, bis-[β-(4-azidosalicylamido) ethyl]disulfide, bis[sulfosuccinimidyl]suberate, dithiobis[succinimidyl proprionate, disuccinimidyl suberate, 1-ethyl-3-[3-dimethylaminopropyl]carbodiimide hydrochloride (EDC), N-hydroxysuccinimide (NHS), riboflavin and any combination thereof; and
   one or more energy sources selected from the group consisting of visible light irradiation, blue light irradiation, ultraviolet irradiation, and any combination thereof.

3. The method of claim 1, wherein at least one property of the hydrogel sealing agent is controlled by at least one selected from the group consisting of a degree of alginate crosslinking, a degree of alginate methacrylation, and a degree of methacrylated alginate crosslinking.

4. The method of claim 1, wherein the alginate is methacrylated at one or more methacrylation sites.

\* \* \* \* \*